(12) United States Patent
Schermeier et al.

(10) Patent No.: US 11,547,515 B2
(45) Date of Patent: Jan. 10, 2023

(54) MOBILE SELECTION SYSTEM AND TREATMENT CARRIAGE

(71) Applicant: FRESENIUS MEDICAL CARE DEUTSCHLAND GMBH, Bad Homburg (DE)

(72) Inventors: Olaf Schermeier, Frankfurt (DE); Kirill Koulechov, Bad Vilbel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 791 days.

(21) Appl. No.: 16/480,685

(22) PCT Filed: Jan. 29, 2018

(86) PCT No.: PCT/EP2018/052150
§ 371 (c)(1),
(2) Date: Jul. 25, 2019

(87) PCT Pub. No.: WO2018/138345
PCT Pub. Date: Aug. 2, 2018

(65) Prior Publication Data
US 2019/0388171 A1    Dec. 26, 2019

(30) Foreign Application Priority Data

Jan. 30, 2017   (DE) .................... 10 2017 201 443.1

(51) Int. Cl.
*A61B 50/13*       (2016.01)
*A61M 1/36*        (2006.01)
(Continued)

(52) U.S. Cl.
CPC .............. *A61B 50/13* (2016.02); *A61B 50/18* (2016.02); *A61M 1/3661* (2014.02);
(Continued)

(58) Field of Classification Search
CPC ... A61B 50/13; A61B 50/18; A61B 2050/185; A61M 1/3661; A61M 2205/3306;
(Continued)

(56) References Cited

U.S. PATENT DOCUMENTS 5,292,029 A  *  3/1994  Pearson  .............. G07F 11/1657
                                                      221/9
6,655,545 B1   12/2003  Sonneborn
(Continued)

FOREIGN PATENT DOCUMENTS

DE         60113129 T2      6/2006
WO      2004053620 A2       6/2004

OTHER PUBLICATIONS

International Search Report and Written Opinion issued in corresponding International Patent Application No. PCT/EP2018/052150 (with English translation of International Search Report) dated Apr. 18, 2018 (15 pages).

(Continued)

*Primary Examiner* — Yazan A Soofi
(74) *Attorney, Agent, or Firm* — Kilyk & Bowersox, P.L.L.C.

(57) ABSTRACT

The invention relates to a mobile selection system for selecting medical accessories comprising a control system, a user interface and a treatment cart. The treatment cart comprises a plurality of storage devices each having at least two storage areas for a respective accessory type. The control system thereby implements a selection method having the following method steps. The treatment identifier of the treatment to be performed is determined in one method step via the user interface. In a further method step, a plurality of accessory set parameters which characterize a medical accessory set are determined on the basis of an accessory database and on the basis of the treatment identifier of the treatment to be performed. The treatment cart (Continued)

Figure 1:
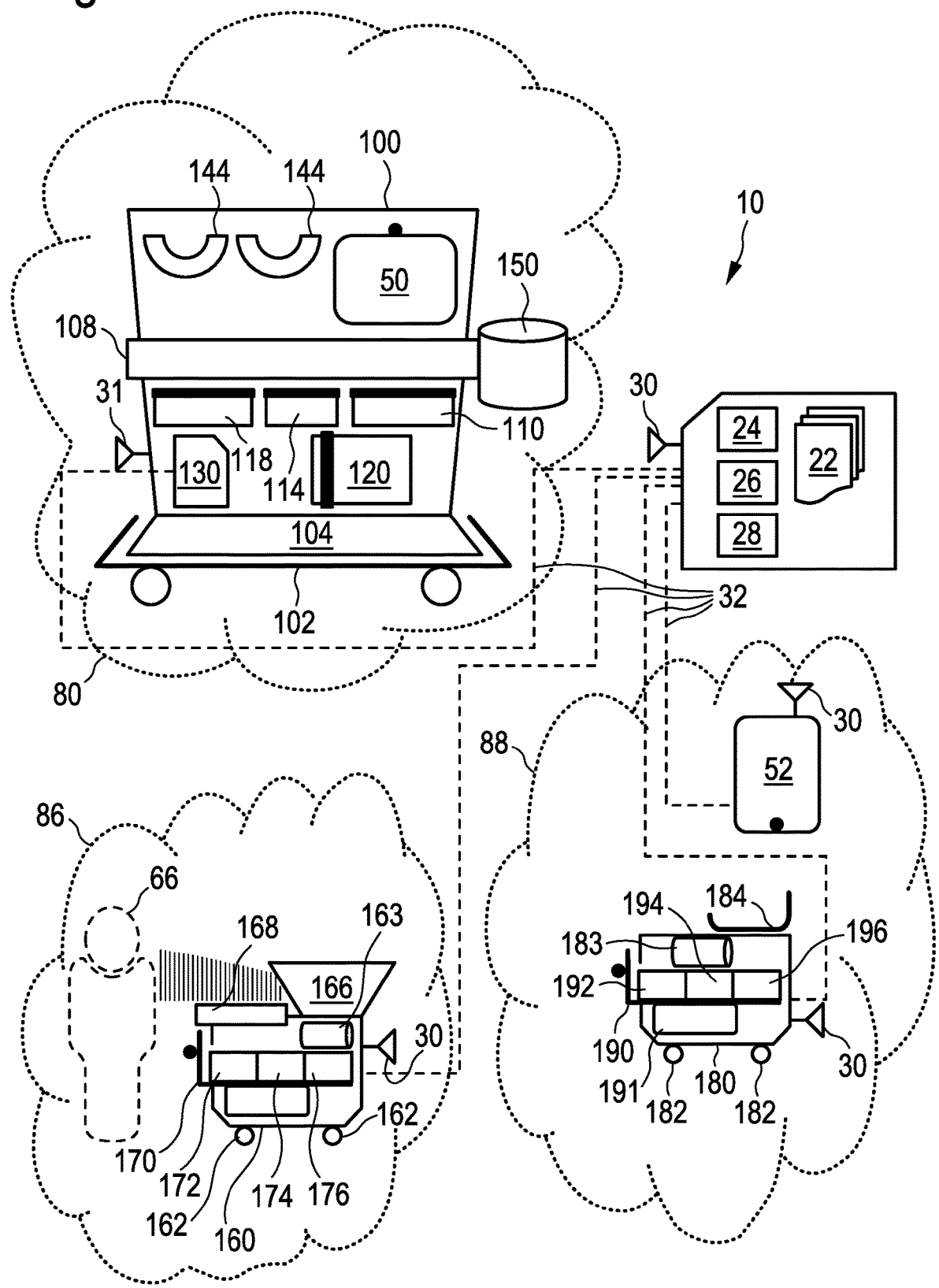

comprises a release mechanism, wherein the control system is designed to control the release mechanism so as to release those medical accessories for which at least one of the storage devices comprises storage area for their accessory types and which are characterized by the accessory set parameters on which the control is based.

17 Claims, 3 Drawing Sheets

(51) Int. Cl.
  *A61B 50/18* (2016.01)
  *B65G 1/137* (2006.01)
(52) U.S. Cl.
  CPC ...... *B65G 1/1373* (2013.01); *A61B 2050/185* (2016.02); *A61M 2205/3306* (2013.01); *A61M 2205/3327* (2013.01); *A61M 2205/3375* (2013.01); *A61M 2205/3393* (2013.01); *A61M 2205/50* (2013.01); *A61M 2205/502* (2013.01); *A61M 2205/52* (2013.01); *A61M 2205/6009* (2013.01); *A61M 2205/6054* (2013.01); *A61M 2205/6072* (2013.01)
(58) Field of Classification Search
  CPC .. A61M 2205/3327; A61M 2205/3375; A61M 2205/3393; A61M 2205/50; A61M 2205/502; A61M 2205/52; A61M 2205/6609; A61M 2205/6054

USPC ........................................................ 700/218
  See application file for complete search history.

(56) References Cited

U.S. PATENT DOCUMENTS

| | | | |
|---|---|---|---|
| 11,344,261 B2* | 5/2022 | Yu ........................ | A61B 5/7275 |
| 2003/0182019 A1 | 9/2003 | Bonini et al. | |
| 2008/0319575 A1* | 12/2008 | Vahlberg ................ | G16H 10/60 |
| | | | 700/242 |
| 2011/0189048 A1 | 8/2011 | Curtis et al. | |
| 2014/0288947 A1* | 9/2014 | Simpson ................ | G16H 10/60 |
| | | | 705/2 |
| 2015/0223890 A1* | 8/2015 | Miller .................... | A61B 50/10 |
| | | | 726/17 |
| 2018/0132966 A1* | 5/2018 | Désaulniers ........... | A61B 90/50 |
| 2019/0388171 A1* | 12/2019 | Schermeier .......... | B65G 1/1373 |
| 2022/0168566 A1* | 6/2022 | Burr .................... | A61N 1/36842 |
| 2022/0172721 A1* | 6/2022 | Tan ..................... | A61M 16/104 |

OTHER PUBLICATIONS

International Preliminary Report on Patentability issued in corresponding International Patent Application No. PCT/EP2018/052150 dated Aug. 8, 2019 (8 pages).

Office Action issued in corresponding German Patent Application No. 10 2017 201 443.1 dated Aug. 14, 2017 (5 pages).

* cited by examiner

MOBILE SELECTION SYSTEM AND TREATMENT CARRIAGE

This application is a National Stage Application of PCT/EP2018/052150, filed Jan. 29, 2018, which claims priority to German Patent Application No. 10 2017 201 443.1, filed Jan. 30, 2017.

The present invention relates to the field of medical technology and/or hospital logistics and in particular to a mobile selection system for selecting medical accessories as well as a treatment cart for such a selection system.

In a treatment, particular medical treatment, of a patient, in addition to the actual treatment itself, it is generally necessary for medical accessories to be provided. One such treatment is in particular a dialysis treatment of a patient which usually needs to be regularly repeated. On the one hand, medical advances have yielded more varied treatments with the accessories thereto required becoming more numerous, diversified and specialized, whereby this can result in increasing expenditure in providing medical accessories for a patient treatment. On the other hand, there is also the increasing desire present in the medical sector, in particular in medical technology and/or hospital logistics, for an optimization and efficient use of resources in the actual medical treatments while maintaining treatment quality at the same or even a higher level. In order to be provided, medical accessories are usually stored in a treatment cart. Such treatment carts are for instance known from the prior art and usually comprise a work surface, drawers, compartments and/or a chassis having wheels or rollers.

The invention is based on the task of providing medical accessories, in particular as regards logistics, improving the selecting of suitable medical accessories and/or the efficient use of medical accessories, increasing treatment safety and/or quality and/or reducing the workload on individuals involved in a patient treatment.

The invention respectively solves this task by a mobile selection system for selecting medical accessories in accordance with the teaching of independent claim 1, a treatment cart in accordance with the teaching of independent claim 14, and a method for selecting medical accessories in accordance with the teaching of independent claim 15. Preferential embodiments, further developments or variants in particular constitute the subject matter of the independent claims. The subject matter of the claims is expressly made a part of the specification disclosure.

A first aspect of the invention relates to a mobile selection system for the selecting of medical accessories, in particular for a cannulation of patient blood vessels and/or for a dialysis treatment. The mobile selection system comprises a control system, a user interface and a treatment cart. The control system comprises an accessory database and a data storage apparatus for the accessory database, wherein the accessory database is designed for data sets on a plurality of medical accessories and is stored on the at least one data storage apparatus. The user interface is designed for one or more inputs of a user, by means of which a treatment to be performed is specified and on the basis of which the control system determines a treatment identifier associated with the treatment to be performed as a result of said inputs. The treatment cart exhibits one or more storage devices, wherein the storage devices have at least two storage areas, each for a respective accessory type from among the plurality of medical accessories. The control system is thereby designed to implement a selection method comprising the following method steps. The treatment identifier of the treatment to be performed is determined in one method step of the selection method. In a further method step of the selection method, one or more accessory set parameters which characterize an accessory set for the treatment to be performed from one or more suitable medical accessories is/are determined on the basis of the accessory database and at least on the basis of the treatment identifier of the treatment to be performed. The treatment cart furthermore comprises at least one release mechanism for releasing medical accessories, whereby the control system is designed to control the at least one release mechanism on the basis of the accessory set parameters such that at least for one of the storage devices, the release mechanism releases those medical accessories for which the storage device has storage area for the accessory type and which are characterized by the accessory set parameters on which the control is based.

Broadly defined, the plurality of medical accessories, the data sets on the plurality of medical accessories and/or the accessory set are not component parts of the mobile selection system according to the invention. Preferably, however, in a narrower interpretation of the accessory set, at least some of the plurality of medical accessories, in particular those medical accessories suitable for a cannulation of patient blood vessels and/or for a dialysis treatment and/or the data sets on the plurality of medical accessories, can be a component part of the inventive mobile selection system or at least a preferential embodiment of the selection system.

In the sense of the invention, a "treatment cart" is to be understood at least as an apparatus which is designed for the storage of medical accessories and for the providing of medical accessories for treatments at a treatment site and is for that purpose provided for the transportation of the medical accessories to the treatment site by means of the treatment cart. Such treatment carts are for instance known from the prior art and usually comprise a work surface, drawers, compartments and/or a chassis having wheels or rollers.

A treatment cart has at least two storage areas for the storing and supplying of medical accessories, preferably for instance a drawer divided into at least two storage areas or a plurality of drawers each having a respective storage area, whereby each storage area is provided for medical accessories of a specific type. In particular, a treatment cart can be equipped with medical accessories for a specific treatment or a specific group of treatments. In particular, a treatment cart can thus store a plurality of medical accessories, whereby the plurality of medical accessories is preselected, in particular presorted, for a specific treatment or a specific group of treatments.

Particularly for a dialysis treatment, such presorting can enable storage of the following medical accessories; i.e. particularly one or more respective medical accessories of a specific accessory type, in storage areas of the treatment cart, and thus their provision for the dialysis treatment. In preparation of the treatment, disposable gloves, in particular disposable gloves of a specific material and of a specific size—the accessory type thus being a disposable glove which is further characterized by its specific material and its specific size—are stored in one storage area and disinfectants and swabs are stored in further storage areas. In particular, further disposable gloves of other sizes or of other materials can thereby be additionally stored in further storage areas. For the cannulation normally required during the dialysis treatment, cannulas, particularly cannulas of a specific type, are stored in one storage area and infusion tubes are stored in another storage area. Moreover, Seldinger wires, catheters and/or adhesive tape for fixing a cannula or catheter can in addition be stored in further storage areas.

Lastly, for post-treatment needs, dressing material, additional swabs—provided other swabs from those used in the preparation are used in the post-treatment—, bandages and/or cooling pads can be stored in further storage areas. It is thereby obvious that if differentiations are made between accessory types, in particular between different types, sizes or materials of one type of medical accessory, for instance cannulas or disposable gloves, the respective medical accessories of such a further, in particular differentiated, accessory type can be stored in further storage areas of the treatment cart.

Preferably, a treatment cart is equipped with at least some of the plurality of medical accessories at a starting location, in particular by means of a pick-and-place system.

For transporting the medical accessories, the treatment cart preferably comprises a transport apparatus, in particular wheels or rollers, or is at least designed for transportation by means of a transport apparatus and in particular connected to the transport apparatus to that end.

Lastly, a treatment cart exhibits spatial dimensions and a weight which allow the treatment cart to be moved within a building, in particular a hospital, ambulatory care unit or a patient's residential building—for instance for home dialysis. Thus, in particular the weight of such a treatment cart, especially when unequipped, amounts at the most to 300 kg, preferably no more than 100 kg, preferably no more than 50 kg, and further preferentially to 20 kg at most. The weight of the treatment cart can thereby increase due to being equipped. The spatial dimensions of such a treatment cart are in particular a length of no more than 2.5 m, preferably no more than 1.5 m, preferably no more than 1 m, and further preferentially at the most 0.5 m, whereby the same applies to the width and height. It is thereby in particular obvious that to transport the medical accessories or to move the treatment cart respectively, such a treatment cart can be configured to be brought into a transporting state which exhibits smaller spatial dimensions than the state for providing the medical accessories.

In the sense of the invention, a "release mechanism" is a mechanism which is designed to release one or more objects, in particular medical accessories. Preferably, the object to be released is thereby initially disposed with a further apparatus and in particular stored in an area of said further apparatus. Preferably, the release mechanism is configured to release the object to be released pursuant to a control.

To realize the releasing, the release mechanism thereby in particular effects a force on a part of the release mechanism, on the object to be released and/or on a part of the further apparatus. To realize the releasing, the release mechanism can also preferably move the object to be released, a part of the release mechanism and/or a part of the further apparatus such that the object is released, thus in particular the object to be released is moved to a supplying area and/or an area, in which the object to be released is located, is made accessible. Such a release mechanism can in particular be designed to open—i.e. in particular pull out—a drawer in which the object to be released is stored, withdraw the object to be released—i.e. in particular extract it from one area and deliver it into the supplying area—and/or open a closure device of the further apparatus which closes off an area containing the object to be released from the surrounding area of the further apparatus—i.e. in particular a lock, a flap or a door of the further apparatus—and thus make accessible an internal area of the further apparatus in which the object to be released is disposed.

Preferably, and alternatively or additionally, the release mechanism is designed to display the area in which the object to be released is stored pursuant to the control. The release mechanism preferably comprises a user interface for said display, in particular for optical output, and/or is designed to send data to such a user interface so as to display the user interface of the further apparatus and/or the area in which the object to be withdrawn is stored. To realize the releasing, the release mechanism can solely effect the display and allow a movement of the object to be withdrawn, or respectively allow access to the object to be withdrawn, or also move the object to be withdrawn or make it accessible as described above for the display. Thus, for instance, the release mechanism can preferably moveably support a part of the further apparatus comprising the area in which the object to be withdrawn is stored as well as comprising a plurality of signal lights, for instance LEDs, by means of which the release mechanism displays the further apparatus in which the object to be withdrawn is stored as well as the area within said apparatus in which the object to be withdrawn is stored, whereby the signal lights can in particular be arranged in the respective apparatus and/or respective area.

The mobile selection system enables selecting, and thereby particularly automatically releasing, medical accessories based on the treatment to be performed, whereby in particular the individuals involved in the treatment are supported and thus their workload reduced and/or sources of error, for instances human errors, can be reduced and thus in particular the treatment safety increased.

The treatment cart can also be equipped with a plurality of medical accessories which are suitable and in particular necessary for a specific treatment or a specific group of treatments, in particular dialysis treatments or a cannulation of blood vessels. The treatment cart and thus the mobile selection system can thereby be advantageously adapted to the changing needs of specific treatments. Thereby, in addition to the physical equipping, the accessory database is in particular also adapted—thus, in particular medical accessory data sets newly created, expanded, modified or deleted—such that the accessory database comprises data sets at least on some and preferably on all of the medical accessories of the plurality of medical accessories with which the treatment cart is equipped. Such a treatment cart thereby enables its own efficient use and/or the efficient use of the medical accessories for different treatments.

One advantage of the storage, providing and/or releasing of the medical accessories by means of the treatment cart can in particular lie in the medical accessories being able to be transported to different treatment sites and released from there. Particularly compared to a fixed arrangement of treatment sites and the medical accessories available there, this allows flexibility in the sites at which a treatment can be performed and/or a patient treated. The individual medical accessories for a specific treatment or a specific group of treatments can also be consolidated into one logistical unit by the treatment cart equipped with said accessories, whereby in particular the transport to a treatment site at which the specific treatment is to be performed can be simplified and/or the safety thereby increased in that individual medical accessories required for the treatment are also in each case actually available at the treatment site for the treatment.

From the accessory database-based selection of the medical accessories suitable for the treatment to be performed, a further advantage, in particular given a plurality of medical accessories, patients and/or treatments, can yield from the selecting of an—in particular particularly—suitable medical accessory and the safety and/or quality of the treatment thereby being increased and/or the medical accessories being used in treatment-specific and/or efficient manner.

Also an advantage of the automated selection of medical accessories suitable for the treatment to be performed based on the accessory database, and in particular the automated releasing by means of the releasing mechanism, can in particular be being able to simplify the realizing of the treatment to be performed, being able to reduce the workload of individuals involved in the treatment and/or being able to reduce sources of error. Moreover advantageously enabled is patients themselves being able to perform simple treatment steps for which the respectively required medical accessories thereto—and in particular only them—are selected and preferably released, whereby personnel can be freed up or patient satisfaction can also be increased due to their active participation.

Lastly, the handling of such a treatment cart and medical accessories can be simplified compared to a conventional treatment cart with medical accessories and in particular by the automated release reducing contact with release-related actuating elements—which conventional treatment carts usually comprise—whereby in particular the hygienics and/or operational efficiency can be increased.

According to one preferential embodiment, the mobile selection system comprises exactly the one treatment cart and some—in particular all—of the components of the mobile selection system are integrated into one physical device unit.

According to one preferential embodiment, a component of the mobile selection system, or preferably a plurality of components of the mobile selection system, is/are in each case separate physical device units. Preferably, at least two of the components of the mobile selection system are disposed at geographically different positions. Preferably the data storage apparatus for the accessory database is thereby positioned at a geographically different location than the treatment cart.

According to one preferential embodiment of the mobile selection system, same comprises at least one further treatment cart. The possible advantages as well as embodiments, further developments or variants of the treatment cart of the mobile selection system also apply correspondingly to the at least one further treatment cart. This thereby advantageously enables the mobile selection system to supply a plurality of treatment sites at the same time. One of the treatment carts can also be equipped for a specific treatment or specific group of treatments and another of the treatment carts equipped for another specific treatment or another specific group of treatments. In so doing, a plurality of medical accessories can advantageously be provided for at least two treatments and preferably for a plurality of treatments, in particular also given a limited storage capacity of the individual treatment carts.

According to one preferential embodiment of the mobile selection system, the control system is designed to allocate one of the treatment carts of the mobile selection system to the user interface. In particular, one or more of the treatment carts can in each case comprise a connecting device for user interfaces which is constructed for a connection, in particular mechanical connection, of the user interface to the respective treatment cart. Preferably, the allocation to one of the treatment carts can thereby be established by the connection of the user interface to the respective treatment cart, in particular by the user interface or the treatment cart comprising a sensor device for detecting the treatment cart or the user interface respectively. Additionally or alternatively, allocation to one of the treatment carts can preferably be specified by means of user input at the user interface. Doing so advantageously enables a treatment cart of the mobile selection system to be allocated to the user interface and allows in particular a plurality of treatment carts of the mobile selection system to be alternatingly used by changing the allocation to the respective treatment cart. Thus, in particular two treatment carts, each equipped for a respective partial treatment of a treatment, can be jointly operated by the user interface. Preferentially, the mobile selection system can also comprise at least one further user interface for inputs specifying the treatment to be performed. The possible advantages as well as embodiments, further developments or variants of the user interface of the mobile selection system thereby also apply correspondingly to the at least one further user interface for inputs for specifying the treatment to be performed. In particular, the mobile selection system can comprise at least as many such user interfaces as it does treatment carts. One advantage of the plurality of user interfaces for inputs to define the treatment to be performed can in particular lie in being able to adapt the operation of the treatment cart and/or treatment carts to the respective need.

According to one preferential embodiment, the treatment cart is of modular construction. The treatment cart thereby comprises a connecting apparatus for treatment cart modules. A treatment cart module is thereby configured, in particular formed, for connection to the treatment cart by means of the connecting apparatus and/or the connecting apparatus is designed, in particular formed, to form a connection with one or more treatment cart modules. Preferably, the connecting apparatus comprises one or more connecting devices for respectively connecting to a treatment cart module. Further preferentially, at least one of the connecting devices comprises or consists of a receiving device, wherein the receiving device is configured to fully or at least partially accommodate a treatment cart module—in particular a treatment cart module corresponding to said receiving device—and thereby establish the connection to the treatment cart.

In addition, the treatment cart preferably comprises one or more of the following treatment cart modules, particularly as further described above and/or in the following: a storage device—in particular a drawer, a compartment, a dosing apparatus such as an adhesive tape dispenser and/or a disinfectant dispenser, a roll holder for adhesive tape rolls or for a roll of pre-portioned, individually packaged bandages and/or a box of gloves—, a user interface—in particular a user interface for inputs to specify the treatment to be performed, a user interface for inputs to specify a treatment step to be performed, a user interface for outputs such as for instance patient data, treatment data or data regarding an actual inventory of medical accessories and/or a user interface for controlling the treatment cart—, a drive apparatus, a reader unit—in particular for patient data, treatment data, user data, RFID identifiers and/or barcodes—, a disposal apparatus, a repository device with a work surface, a camera module and/or laboratory equipment. Further possible and preferential treatment cart modules are described elsewhere herein.

Preferably, the mobile selection system, in particular the control system and/or the treatment cart, has an allocation rule for treatment cart modules and a data storage apparatus for same, wherein the allocation rule for treatment cart modules is configured to assign a treatment cart a treatment cart module on the basis of allocation data stored in the data storage apparatus for said allocation rule. Further preferentially, the allocation of the treatment cart module to one of the treatment carts can thereby be established by the connection of the treatment cart module to the respective treatment cart, in particular by the treatment cart module or the treatment cart comprising a sensor device for detecting the treatment cart or the treatment cart module respectively and by identifying corresponding allocation data written in the data storage apparatus for the allocation rule for treatment cart modules. This allocation, which can in particular be automated by means of the detection process, enables the mobile selection system and in particular the control system to also select medical accessories based on the allocation and/or perform a control based on the allocation and in particular control the at least one release mechanism of the treatment cart on the basis of the allocation. Thus, should the treatment cart comprise a dosing apparatus for adhesive tape as a treatment cart module, a section of adhesive tape can for instance be selected from an adhesive tape and the dosing apparatus for adhesive tape be actuated to release such an adhesive tape section or else select a previously cut, individually packaged adhesive strip section which is for instance stored in a drawer of the treatment cart and actuated the at least one release mechanism to open said drawer.

According to one preferential embodiment, at least one first of the storage devices of the treatment cart comprises or consists of a drawer, in particular a tray, whereby the drawer has exactly one storage area for one accessory type of the plurality of medical accessories. In an alternative variant, the drawer can thereby also be divided into a plurality of storage areas for different accessory types. Additionally, at least one second of the storage devices of the treatment cart comprises or consists of a drawer or a compartment, same in turn having exactly one storage area for one accessory type or, alternatively, a plurality of storage areas for different accessory types. The treatment cart hereby exhibits a total of at least two storage areas, each for a respective accessory type, so that storage and thus selection between the medical accessories of the two accessory types is enabled. In the context of the present embodiment, the plurality of medical accessories thereby consists only of the accessory types for which the first or the second storage devices comprises storage areas or, alternatively, the treatment cart comprises even further storage devices for the further accessory types of the plurality of medical accessories corresponding to the first or the second storage device and/or, in a mobile selection system having multiple treatment carts or additional storage areas which are not part of a treatment cart, each of the treatment carts or additional storage areas is associated with a part of the plurality of medical accessories by means of the accessory database and stored there accordingly.

In a preferential fully automated variant, the treatment cart comprises a further release mechanism, wherein the at least one release mechanism is designed to release medical accessories from the drawer of the first storage device and the further release mechanism is designed to release medical accessories from the drawer/compartment respectively of the second storage device. This advantageously enables the automatic releasing of medical accessories of all the accessory types stored in the treatment cart.

According to an alternative and preferential semi-automated variant, the treatment cart is not configured to automatically release medical accessories from the second storage device and, in particular, does not have the further release mechanism. This advantageously enables the medical accessories of the accessory types stored in the first storage device to be automatically released while the medical accessories of the accessory types stored in the second storage device cannot be extracted automatically and/or independently of the control by the control system. This can simplify the technical implementation and/or the use of the treatment cart and thus the mobile selection system. Thus, particularly the medical accessories of an accessory type which are only to be released pursuant to selection—for instance cannulas—can be stored in the first storage device while medical accessories of other accessory types—for instance disinfectants, swabs, bandages and/or disposable gloves—are stored in the second storage device. Access to critical medical accessories such as e.g. cannulas can also be limited to authorized users, in conjunction with a user authorization, while other medical accessories such as for instance disinfectants, swabs, bandages and/or disposable gloves are made generally available.

Preferably, at least one of the release mechanisms can comprise or consist of a motorized cable pull with which the drawer can be pulled out to release medical accessories and then subsequently pushed back in again.

According to one preferential embodiment, the treatment cart comprises one, in particular only one, storage device having at least two storage areas, each for one accessory type. Said storage device can in particular comprise or consist of a drawer divided into at least two storage areas.

One advantage of grouping a plurality of storage areas into one storage device, in particular one drawer, can in particular be that of being able to reduce the number of storage devices and thus in particular the complexity of the release mechanism and/or the number of steps, in particular movements, required to release an accessory set. In particular, medical accessories of some, preferably all, of the accessory types stored in the drawer can be released by pulling out said drawer.

One advantage of dividing multiple storage areas among multiple storage devices, preferably multiple drawers, can in particular be in enabling access only to the medical accessories of the accessory set and, in particular, only pulling out that respective drawer in the process of releasing the medical accessories which has storage areas for the accessory types of the medical accessories of the accessory set.

According to one preferential embodiment of the treatment cart in which the treatment cart comprises at least one drawer and one of the drawers comprises at least two storage areas, the control system can be configured so as to control the release mechanism for this drawer such that the release mechanism only pulls the drawer out of a receiving device for the drawer far enough that one of the at least two storage areas in which the medical accessories of the accessory set is stored is pulled out of said receiving device, while further storage areas arranged behind said storage area with respect to the direction of movement occurring during the extending out are not pulled out of the receiving device. This thereby advantageously enables limiting access to the medical accessories on the one hand and, on the other, reducing the number of storage devices needed to store a specific number of accessory types.

According to one preferential embodiment, the treatment cart comprises a disinfectable work surface. In particular, the work surface can comprise or consist of a supplying area. One advantage of the work surface can in particular be that at least some or preferably all of the medical accessories of the accessory set can be placed on the work surface prior to the treatment, wherein they are available for the treatment, without a releasing and/or an actuating being required to release and/or extract said medical accessories during said treatment. This can in particular improve the hygienics.

In one embodiment comprising a work surface, the at least one release mechanism or a further release mechanism of the treatment cart can also comprise or consist of a separating apparatus configured for at least one of the storage devices so as to extract from the respective storage areas those medical accessories for which the storage device has storage area for their accessory types and which are characterized by the accessory set parameters on which the control is based and place them on the work surface or the supplying area respectively. This advantageously enables medical accessories to be segregated from the respective storage areas and in particular thus provided without access needing to be provided to the storage area for the respective accessory type and/or no actuation for release and/or manual extraction being needed, in particular during the treatment. This can in particular improve the hygienics. The segregation can thereby take place prior to the treatment. The segregation can also occur during the treatment and preferably occur as a function of a respective treatment step of the treatment to be performed. In particular, such a concerted segregating of the respectively required medical accessories to the treatment step can further simplify the executing of the treatment to be performed.

According to one preferential embodiment, the mobile selection system and in particular the treatment cart, or one of the treatment carts respectively, is configured for an assist function. Such an assist function supports a user, particularly the user of the treatment cart and/or an individual involved in the treatment, in executing the treatment to be performed and, particularly when the treatment to be performed comprises a plurality of treatment steps and/or partial treatments, in the respective executing of said treatment steps.

The mobile selection system, preferably the control system, is in particular also designed to determine the respective treatment to be performed and particularly the respective treatment step to be performed. In order to determine the treatment step to be performed, the mobile selection system can in one variant comprise a user interface configured for one or more inputs from the user, by means of which the treatment to be performed and particularly the treatment step to be performed is specified and on the basis of which the control system determines the treatment to be performed and particularly a treatment step identifier associated with the treatment step to be performed resulting from the inputs. In one preferential additional or alternative variant, the mobile selection system, in particular one of the treatment carts, can comprise a detection system for treatments in order to determine the treatment step to be performed, same detecting an individual involved in the treatment, a medical accessory, in particular the accessory set, and/or their arrangement and/or movement relative to each other by means of sensor technology-based measurement of radiation, in particular light, ultrasound, weight and/or inertia and, based on that, determines the treatment to be performed and/or the treatment step to be performed next.

Preferably, one of the user interfaces of the mobile selection system is designed to output assistance information for the assist function or the mobile selection system comprises an additional user interface designed thereto. Preferably, one of the treatment carts exhibits this user interface, whereby it can in particular be designed as a treatment cart module. Such assistance information can in particular be acoustic or visual instructions on the treatment to be performed, the steps of the treatment, the treatment step to be performed and/or the medical accessories and/or can moreover be how the treatment or the treatment step is to be respectively performed in each case and/or how a specific medical accessory is to be used in particular for the treatment or the treatment step. Preferably, the control system comprises a data storage apparatus for assistance information and is designed to run an assist process comprising at least the following method steps. In one method step of the assist process, the treatment to be performed, the treatment step to be performed and/or a medical accessory for same is determined by the treatment detection system. In a further method step of the assist process, corresponding assistance information is thereby read from the data storage apparatus for assistance information and output to the assist function user interface.

The control system can also preferably be configured to run an assist process which comprises at least the method step of: Determining one or more assist parameters which characterize the treatment to be performed, the treatment step to be performed and/or a medical accessory for same by means of the treatment detection system. Additionally, in a preferential variant, the control system is designed to control the at least one release mechanism based on the accessory set parameter and the assist parameter so as to release that medical accessory of the accessory set required for the treatment step to be performed and/or which is to be used after the medical accessory currently being used. In a preferential alternative or additional variant, the at least one release mechanism is designed to release the medical accessories as a function of the assist parameters.

The following will in particular describe preferential further developments of the mobile selection system and its components which can in each case be combined at will by the skilled expert to the extent that doing so is technically possible and not expressly excluded. Correspondingly, the preferential further developments can in particular also be combined with preferential embodiments.

According to one preferential further development, one of the storage devices comprises or consists of a drawer, in particular a tray, having one or more storage areas each for a respective accessory type of the plurality of medical accessories. Additionally, the at least one release mechanism or a further release mechanism of the treatment cart for this storage device is designed to open the drawer. To that end, in one preferential variant of the release mechanism, the drawer or the storage device comprises a locking device for the drawer, preferably for instance a bolt and a counterpiece or a magnetic latch, and the release mechanism is designed to unlock the locking device. In one preferential additional or alternative variant, the release mechanism is designed to pull out the drawer, for instance by means of a motorized cable pull or thread or, after unlocking, by means of a drawer bearing acting in conjunction with the force of gravity.

One advantage of the drawer can in particular be that of different medical accessories being able to be stored in the storage areas of said drawer, in particular sorted according to their accessory type, and that after being released from the storage areas, being able to be removed by the user, particularly in systematic manner. Compared to just simply displaying where the accessories to be released are stored and/or the opening of the drawer without it being pulled out, the releasing by means of extending out the drawer enables improving the selecting of the medical accessories for the treatment to be performed and in particular increasing user convenience, hygienics and/or the operational efficiency since the user is able to eliminate having to perform additional work steps in selecting the medical accessories and/or opening the drawer.

One advantage of a variant in which the storage device comprises exactly one storage area for medical accessories of exactly one accessory type can in particular be that only medical accessories of said accessory type are made available when the drawer is opened, whereby in particular treatment safety can be increased and/or the systematic withdrawal of suitable medical accessories simplified and/or accelerated.

One advantage of a variant in which the storage devices comprise at least two storage areas can in particular be that of being able to reduce the number of storage areas and thereby in particular the complexity of the release mechanism and/or the number of work steps, in particular movements, required in releasing an accessory set.

According to one preferential further development, one of the storage devices comprises a cover system for at least one storage area of the storage device. The cover system is designed to cover said storage area during the releasing of medical accessories from the storage device provided no medical accessory is to be released from said storage area and, otherwise, uncover said storage area. According to one preferential variant, the cover system comprises a cover element for the storage area. According to one preferential and alternative or additional variant in which the storage device comprises a drawer with at least two storage areas, a frame or receiving device for the drawer is designed as a component part of the cover system and the control system, the drawer is only extended far enough out of the frame or receiving device that those areas of the at least two storage areas in which the medical accessory to be released is stored is pulled out while further storage areas arranged behind the storage area relative to the direction of movement during the extending out is not pulled out of the frame or receiving device respectively. This advantageously enables limiting access to the medical accessories. Compared to access restriction via the respective storage devices for the individual accessory types, the number of storage devices needed to store a specific number of accessory types can also be reduced.

According to one preferential further development, the at least one release mechanism or a further release mechanism of the treatment cart comprises or consists of a separating apparatus for one of the storage devices. The separating apparatus is thereby designed to segregate medical accessories out of at least one of the storage areas of the given storage device. In addition, the control system is designed to control the separating apparatus on the basis of the accessory set parameter such that the separating apparatus extracts at least one medical accessory out of the at least one storage area of said storage device and delivers it to a supplying area when the accessory set parameter characterizes such an medical accessory.

A "separating apparatus" in the sense of the invention is an apparatus which is designed to extract an object, in particular a medical accessory, at a starting location, in particular from a storage device and/or from a storage area of a storage device, and release it at a target location, in particular at a supplying area.

To that end, the separating apparatus preferably comprises guide means, in particular control devices, which control the starting location or the target location. By controlling the starting location, a specific object can be extracted from a plurality of objects which can in particular be stored in a storage device or a storage area of a storage device. The control of the target location in addition allows delivering the object which is to be segregated to a specific destination, in particular to a specific position within a supplying area. Preferably, such a control means even guides the object to be segregated in a specific direction. Also preferentially and alternatively or additionally, such a control means influence or controls a guide means such that said guide means guides the object to be segregated from a specific starting location and/or to a specific target location. Such control means, control devices respectively, are in particular variable magnetic fields or electric fields, a flow of air controllable in its strength and/or direction, switches—for instance in the case of rails—, flaps and/or actuators.

In particular, the separating apparatus can also be designed as a gripper device: wherein the guidance device comprises one or more gripping members of the gripper device and the control device comprises or consists of a positioning and/or orientation device of the gripper device—for instance telescopic rods and/or articulated joints and/or hinged arms.

The further development with a separating apparatus enables at least one medical accessory to be segregated out from the at least one storage area. Such a medical accessory can thus in particular be advantageously released and/or provided such that no release actuation and/or manual extraction is required, particularly during the treatment. Also in particular able to be avoided is needing to make the storage area for the accessory type of the medical accessory accessible during the release process. Hygienics can thus be improved and the convenience of use and/or the operational efficiency increased.

According to one preferential variant of the further development with a separating apparatus, the separating apparatus is configured as an automatic dispenser apparatus for medical accessories such as disposable gloves, cannulas, syringes, swabs, wipes or pre-portioned bandages or adhesive tape sections. Such medical accessories can in particular be individually packaged, for instance in the case of bandages, swabs or cannulas, or be packed into units each of a predetermined number greater than one such as for instance a pair of disposable gloves. In the case of such packaged medical accessories, the automatic dispenser apparatus can preferably comprise a cutting device for cutting or a tearing device for tearing open medical accessory packaging.

The treatment cart can also comprise one or more manual dispenser apparatus for medical accessories according to one preferential further development. In particular, such a manual dispenser apparatus is not controlled by the control system but rather manually operated. According to one preferential variant, a manual dispenser apparatus comprises a chute for storing medical accessories of a specific accessory type. When the manual dispenser apparatus is oriented for its usual use, the longitudinal axis of the chute points at least so far along the gravitational forces that the medical accessories stored there can fall or slide downward. The manual dispenser apparatus thereby moreover comprises a support piece and the chute a lateral opening for the removal of medical accessories, whereby the support piece is designed so as to support the lowest medical accessory such that the lowest medical accessory will be held in the chute and at the opening, will able to be removed through the opening, and so as to block the opening to further medical accessories, in particularly those disposed above the lowest medical accessory and prevent the further medical accessories from falling or sliding downward.

According to one preferential further development, the treatment cart has a dosing apparatus comprising one of the storage devices having at least one storage area for at least one medical accessory of a dosable accessory type and a separating apparatus for extracting part of the at least one medical accessory. Preferably, the separating apparatus is thereby also configured as a component part of the release mechanism or the release mechanism is configured as the separating apparatus. The selection method of the preferential further development further comprises the following method steps. One method step checks whether the accessory set parameters characterizes a medical accessory of the dosable accessory type. Should this be the case, a further method step determines one or more dosing parameters characterizing the medical accessory and the required dosage for the accessory set. In addition, the control system is designed to control the separating apparatus of the dosing apparatus on the basis of the dosing parameter and preferably the accessory set parameter such that the separating apparatus extracts a portion of the at least one dosable medical accessory corresponding to the required dosage from the at least one storage area of the dosing apparatus and dispenses it to a supplying area. Doing so advantageously enables extracting the respectively required portion of a dosable medical accessory. The need to stock a plurality of different dosages of a medical accessory type can in particular thereby be eliminated.

According to one preferential variant, to extract the dosable medical accessory, a portion thereof is detached, in particular cut off. Preferably, this variant comprises a cutting device and a holding device in the storage area for the dosable medical accessory. Particularly in the case of a dosing apparatus for adhesive tape rolls, same can comprise a blade with an actuator as the cutting device, an adhesive tape roll holder for adhesive tape rolls as the holding device, and additionally a conveyor device for adhesive rolls. This thereby advantageously enables detaching a respective part of the dosable medical accessory, in particular an adhesive tape of the adhesive tape roll, according to need, whereby different dosages of the dosable medical accessory can be provided without needing to be individually stocked. Particularly pre-portioned—thus in particular pre-cut—medical accessories are usually more expensive than a medical accessory able to be sectioned into such pre-portioned medical accessories. Such sectioning can therefore in particular reduce costs. In particular, the number of storage areas can also be reduced and/or the segregating technically simplified compared to segregating from a plurality of storage areas for a plurality of dosages.

According to one preferential and alternative variant for a flowable, fluid, pasty, powdery or granular medical accessory, the storage device of the dosing apparatus has a container comprising the at least one storage area which is designed to accommodate the flowable medical accessory and the separating apparatus is designed to allow a predetermined volume of the flowable medical accessory to flow out of the container, in particular be pumped out, pursuant to the dosing parameter. Preferably, the separating apparatus comprises a pump device and/or a controllable valve, in particular an electrically controllable valve, to that end. In particular, such flowable medical accessories are particularly suited to being dosed. One advantage of dosing by allowing the flowable medical accessories to flow can in particular lie in the technically simple realization of same; i.e. in particular a realization with few and/or proven components—such as pumps and/or valves—and/or in the reliability of such a realization. In particular, a dosing apparatus of this variant can dispense a portioned volume of a disinfectant or cleansing agent, wherein the volume dispensed can in particular be fixedly preset or dependent on the treatment to be performed or the treatment step to be performed, and whereby the hygienics, the treatment safety and/or the operational efficiency can be increased.

Preferably, the treatment cart can comprise a combination of a separating apparatus for swabs or wipes and a dosing apparatus for disinfectants, wherein the dosing apparatus applies a dose of disinfectant on a selected or to be selected swab or wipe.

According to one preferential further development, the treatment cart comprises a disinfectable work surface or a repository device having a disinfectable work surface. The work surfaces are thereby designed for the depositing of medical accessories and/or comprise one or more supplying areas for the sorting of medical accessories.

One advantage of the disinfectable work surface can be in particular be in it being able to be disinfected, whereby in particular the hygienics can be ensured even over longer periods of using the treatment cart and/or the work surface or the repository device respectively can be used for multiple treatments.

One advantage of the work surface configured for the depositing of medical accessories can in particular lie in being able to place at least some or preferably all of the medical accessories of the accessory set on the work surface prior to the treatment, wherein they are available for the treatment, without a release and/or an actuation to effect release and/or a extracting of such medical accessories being necessary during the treatment. This can in particular increase operational efficiency and treatment safety and/or, in particular together with the disinfectability of the work surface, improve the hygienics.

One advantage of the work surface having one or more supplying areas can in particular lie in a medical accessory, when it is sorted out onto one of these supplying areas, being able to be placed onto the work surface and in particular be supported by the repository device, whereby the hygienics, the treatment safety and/or the operational efficiency can be improved. Preferably, the work surface comprises a plurality of supplying areas and a plurality of separating apparatus of the treatment cart are configured to separate medical accessories onto a respective specific supplying area such that a medical accessory of a specific accessory type is always separated onto a specific supplying area and in this way made available there. This thereby advantageously enables specific supplying areas to be associated with specific accessory types so that in particular the position of the medical accessories of a specific accessory type always remains constant on the work surface and/or medical accessories of different accessory types can be differentiated due to their different positions on the work surface, whereby in particular individuals involved in the treatment can be freed up and the operational efficiency and/or treatment safety increased.

According to one preferential further development, the mobile selection system, in particular the treatment cart, comprises a disinfecting apparatus for the treatment cart, in particular for a work surface of the treatment cart. According to a preferential variant, the control system is designed to control the disinfecting apparatus for the work surface such that the disinfecting apparatus disinfects the work surface in particular before, during and/or after the treatment to be performed and/or before, during and/or after specific treatment steps of the treatment to be performed.

According to one preferential further development, the treatment cart comprises a connecting apparatus for treatment cart modules. The connecting apparatus is thereby configured to establish a form-fit, force-fit and/or material-bond connection between the treatment cart and one or more treatment cart modules.

As defined by the invention, a "treatment cart module" is an apparatus for a treatment cart which can be detached from the treatment cart and provides one or more functions for the treatment carts. In particular, the treatment cart module can be detachably connected in form-fit and/or force-fit manner to the treatment cart and, at least when connected together, assume one or more functions of the treatment cart and/or expand the treatment cart's range of functions. Preferably, such a treatment cart module comprises one or more connection points for a detachable, in particular mechanical, connection to the treatment cart, in particular to a connecting apparatus of the treatment cart.

As defined by the invention, a "connecting apparatus for treatment cart modules" is an apparatus for detachably connecting one or more treatment cart modules to a treatment cart. Preferably, the connecting device is a component of the treatment cart and connected mechanically to same. The detachable connection can in particular be a form-fit or force-fit connection, whereby it is preferably a mechanical connection. Preferably, the connecting apparatus comprises one or more connecting devices, each for one treatment cart module. Such a connecting device is thereby configured and in particular formed to establish, in particular form, a detachable, in particular mechanical connection to one or to a plurality of connection points of the respective treatment cart module. Further preferentially, at least one of the connecting devices comprises or consists of a receiving device, whereby the receiving device is designed to wholly or partially accommodate a treatment cart module—in particular a treatment cart module corresponding to the receiving device—and thus establish the detachable connection to the treatment cart.

One advantage of the modular structure to the treatment cart can in particular be being able to adapt the treatment cart to the respective requirements by means of the corresponding treatment cart modules. Such a treatment cart also enables simple repairs and/or upgrades by way of replacing treatment cart modules, whereby in particular service life can be extended.

According to one preferential further development, the treatment cart comprises a bus system for establishing a data connection to, and in particular for the control of, at least one of the treatment cart modules, the at least one release mechanism or a further release mechanism, the separating apparatus and/or the dosing apparatus. Such a bus system can in particular be a universal serial bus (USB) or a controller-area network bus (CAN bus).

According to one preferential further development, the user interface, at least one of the storage devices, one of the release mechanisms or a part thereof, the control system or a part thereof, a drawer of one of the storage devices, the separating apparatus, the dosing apparatus and/or the repository device is configured as a treatment cart module.

Preferably, a treatment cart module comprises a combination of user interface, at least one of the storage devices, one of the release mechanisms or a part thereof, the control system or a part thereof, a drawer of one of the storage devices, the separating apparatus, the dosing apparatus and/or the repository device and/or further apparatus.

According to one preferential further development, the treatment cart comprises a connecting apparatus for a transport apparatus detachable from the treatment cart. In particular, the detachable transport apparatus can be designed as a treatment cart module. Even in a broad interpretation, the detachable transport apparatus is not a component part of the treatment cart. Preferably, however, the treatment cart can comprise the detachable transport apparatus.

In the sense of the invention, a "transport apparatus" is an apparatus which is designed to movably support a further apparatus, in particular a treatment cart, on a pavement surface, in particular the ground. Preferably, the transport apparatus is to that end mechanically connected to the further apparatus. Said connection can thereby either be permanent or disconnectable; the transport apparatus thus being a detachable transport apparatus. For the movable support on the ground, for instance a floor or a street, the transport apparatus can preferably comprise wheels, rollers, belts or chains. Preferably, the transport apparatus can be an active transport apparatus and to that end comprise a drive—in particular a motor which is mechanically coupled to at least one of the wheels. Preferentially and alternatively, such a transport apparatus can be a passive transport apparatus, thus having no drive. Further preferentially, such a transport apparatus can be an autonomous transport apparatus comprising a drive and a control device and being designed to travel from a starting point to a destination autonomously; i.e. in particular without human control.

According to one preferential further development, the user interface is non-detachably connected to the treatment cart. Said connection is thereby a non-detachable, form-fit, force-fit or material-bond connection. The user interface is also preferably integrally connected to the treatment cart. This thereby advantageously particularly enables the operability of the user interface, and thus the treatment cart itself, at the treatment cart's location.

According to one preferential further development, the user interface is detachably connected or connectable to the treatment cart, in particular in detachable form-fit or detachable force-fit manner. One advantage of the detachable connection of the user interface can in particular lie in the user interface being able to be detached from the treatment cart and being able to be cleaned, in particular separately from the treatment cart, and/or being able to be replaced by another corresponding user interface, for instance in the case of defect. It is in particular also possible for the treatment cart and the user interface to be combined into one logical unit, provided they are still detachably connected to one another.

According to one preferential further development, when the user interface is designed at least for inputs in consequence of which the control system determines the treatment identifier of the treatment to be performed, said user interface is positioned or positionable at a different geographical location as the location of the treatment cart. This advantageously enables the treatment cart to be operated independently of the location of the user interface. Thus, prior to or during treatment, for instance, the user interface can be positioned at a location which is particularly suited to operating the treatment cart during the treatment.

According to one preferential further development, the mobile selection system comprises at least one further treatment cart. The possible advantages as well as embodiments, further developments or variants of the treatment cart of the mobile selection system thereby apply correspondingly to the at least one further treatment cart.

According to one preferential further development, in particular with a preferential further development of the mobile selection system having one or more treatment carts and/or one or more treatment cart modules, at least one of the treatment cart modules, or the treatment cart module respectively, can be allocated to at least one of the treatment carts.

One advantage of the allocatable treatment cart module can in particular be in that the treatment cart—particularly in a mobile selection system having only one treatment cart or in an embodiment, further development or variant of the treatment cart—or one of the treatment carts respectively—particularly in a mobile selection system having a plurality of treatment carts—can be allocated to the allocatable treatment cart module, whereby it can in particular be determined whether the treatment cart comprises said allocatable treatment cart module. In one preferential variant, the control system is thereby designed to control a treatment cart as a function of which allocatable treatment cart modules are assigned to the treatment cart and/or which treatment cart modules it comprises.

Conversely, one advantage of the allocatable treatment cart module, in particular with a mobile selection system having multiple treatment carts, can be that of one of the treatment carts being associated with the allocatable treatment cart module, whereby it can in particular be determined whether or not and which of the treatment carts comprises said allocatable treatment cart module. In one preferential variant, the allocatable treatment cart module is thereby advantageously designed such that its functions adapt to the treatment cart comprising said treatment cart module.

According to one preferential further development in which at least one treatment cart module can be assigned to a treatment cart, the mobile selection system, in particular the control system, comprises an allocation rule for treatment cart modules and a data storage apparatus for same. The allocation rule is thereby configured to allocate, based on allocation data stored in the data storage apparatus, a treatment cart module characterized by a treatment cart module identifier to a treatment cart characterized by a treatment cart identifier. One advantage of the allocation rule for treatment cart modules can in particular lie in the allocation between treatment cart modules and treatment carts being able to be determined on the basis of allocation data stored in the data storage apparatus for the allocation rule. Preferably, the stored content of said data storage apparatus can be modifiable, thus the data storage apparatus has at least one writable, in particular rewritable, memory area, so that an allocation can be changed by changing the allocation data. This in particular enables adapting the allocations of the allocation rule to the actual physical circumstances—in particular without mechanical modifications and/or at least substantially without wear.

According to one preferential further development in which at least one treatment cart module can be allocated to a treatment cart, the mobile selection system or the treatment cart comprises a user interface designed for one or more user inputs, by means of which the allocation of the allocatable treatment cart module to the treatment cart is established.

According to one preferential variant, the control system is thereby designed to determine allocation data on the basis of the input and write to the allocation rule storage apparatus for treatment cart modules which treatment cart module allocation identifies the treatment cart.

According to one preferential further development in which at least one treatment cart module can be allocated to a treatment cart, the treatment cart comprises a detection system for treatment cart modules which gathers data on a treatment cart module in particular adjacent to the detection system by means of sensor technology-based measurement of radiation, in particular electromagnetic radiation such as light or radio waves, ultrasound, electrical contacts and/or at least substantially static magnetic fields and, based on that, determines the treatment cart module identifier of the treatment cart module and/or allocates said treatment cart module to the treatment cart.

For the allocation, the detection system is preferably configured to establish a data link to the control system and/or comprises a data connection to the control system, whereby the detection system or the control system is designed to determine the treatment cart identifier of the treatment cart as well as determine allocation data on the basis of the treatment cart identifier and the treatment cart module identifier and write to the allocation rule storage apparatus for treatment cart modules which characterize the allocation of the treatment cart module to the treatment cart. In one preferential variant, the at least one allocatable treatment cart module comprises an identifier device, in particular a bar code or an RFID tag, and the detection system for treatment cart modules comprises a corresponding reader unit, in particular a bar code reader and/or RFID reader, with which the treatment cart module and/or the treatment cart module identifier can be determined.

According to one preferential further development, at least one treatment cart module comprises a detection system for treatment carts. Same is configured analogously to the detection system for treatment cart modules, wherein a treatment cart and/or its treatment cart identifier can be determined on the basis of measurement. The possible advantages as well as embodiments, further developments or variants of the detection system for treatment cart modules thereby apply correspondingly to the detection system for treatment carts.

According to one preferential further development in which at least one treatment cart module can be allocated to a treatment cart, the allocation between the treatment cart module and the treatment cart is determined by the establishing of the detachable connection. One advantage of the allocation via detachable connection can in particular lie in the allocation being able to be automated and/or no further work steps being required apart from establishing the detachable connection, whereby in particular personnel can be freed up, errors prevented and/or operational efficiency increased.

Preferably, the allocation can thereby be made mechanically, in particular by connecting to a mechanical control element of the treatment cart and/or by connecting to a bus system of the treatment cart, this advantageously allowing a technically simple realization.

The allocation can also preferably be made by means of a detection system for treatment cart modules which is designed to perform the identification during or after the detachable connection having been made, which advantageously allows automated allocation. According to one preferential variant, the treatment cart modules do not need to be specially configured for this identification or only have a technically simple, proven and/or economical identifier device—for instance a bar code or an RFID tag—whereby the technical complexity for the identification can be shifted to the detection system, which in particular enables treatment cart modules to be technically simpler, more economical and/or more reliable.

According to one preferential further development, the mobile selection system comprises at least one further user interface. The possible advantages as well as embodiments, further developments or variants of the user interface of the mobile selection system thereby apply correspondingly to the at least one further user interface.

According to one preferential further development in which the mobile selection system comprises at least one further treatment cart, at least one of the user interfaces can be allocated to the treatment cart and the further treatment cart for inputs. One advantage of the allocatable user interface can in particular be it being able to be allocated to one of the treatment carts, whereby it can in particular be defined which of the treatment carts will be served by the user interface and/or for which treatment cart this user interface will acquire user inputs by means of which in particular a treatment to be performed is determined for which this treatment cart releases medical accessories.

According to one preferential further development in which at least one of the user interfaces can be allocated to one of the treatment carts, the user interface is non-detachably connected to one of the treatment carts and thereby allocated to said treatment cart. One advantage of the allocation by way of non-detachable connection can in particular be that of being able to realize the allocation in a technically simple manner and/or it being particularly sturdy and/or reliable, particularly compared to an adaptable allocation or a detachable connection.

According to one preferential further development in which the mobile selection system comprises at least one user interface which is non-detachably connected to one of the treatment carts and thus allocated to same, the mobile selection system comprises at least one such non-detachably connected user interface for each of the treatment carts, same then thereby being allocated to the respective treatment cart.

According to one preferential further development in which at least one of the user interfaces is allocatable to one of the treatment carts, the user interface is detachably connected to one of the treatment carts and thereby allocated to said treatment cart. One advantage of the allocation by way of detachable connection can in particular be that of being able to realize the allocation in a technically simple manner and/or, particularly compared to an allocation by way of non-detachable connection, the user interface being able to be adaptively allocated to one of the treatment carts by the detachable connection in terms of the respective requirements.

According to one preferential further development in which at least one of the user interfaces can be assigned to one of the treatment carts, the control system comprises to that end an allocation rule for user interfaces and a data storage apparatus for same. The allocation rule is thereby configured to allocate, based on allocation data stored in the data storage apparatus, a user interface characterized by a user interface identifier to a treatment cart characterized by a treatment cart identifier. One advantage of the allocation rule for user interfaces can in particular lie in the allocation between user interfaces and treatment carts being able to be determined on the basis of allocation data stored in the data storage apparatus for the allocation rule for user interfaces. Preferably, the stored content of said data storage apparatus can be modifiable, thus the data storage apparatus has at least one writable, in particular rewritable, memory area, so that an allocation can be changed by changing the allocation data. In one preferential variant, at least one of the user interfaces is designed for one or more user inputs, by means of which the allocation of at least one of the user interfaces, as allocatable by means of the allocation rule, to a treatment cart is established and the control system is designed to determine allocation data on the basis of the inputs and write to the allocation rule storage apparatus which characterizes the allocation of said at least one allocatable user interface to the treatment cart.

According to one preferential further development, the control system is designed to clearly differentiate among users and/or patients, in particular individuals involved in the treatment. A patient or a user is preferably uniquely identified by the control system. Preferentially, multiple users or multiple patients can also be grouped and the patient groups and/or user groups uniquely identified by the control system. In addition, the control system can also consolidate non-identified patients or users into a non-identified group. In the identification, the control system preferably processes identification data. Preferably, the control system comprises a data storage apparatus for identification data and is designed to perform an identification procedure which verifies the identity of a patient or a user and identifies the patient or user if data stored in the data storage apparatus for identification data corresponds to the patient or user.

Identification data comprises for example a login text and a password text or a data set for facial recognition or for an iris scan or fingerprint scan or other data or biometric data. Biometrics offers the advantage that the identity of the patient or user can be determined without cognitive activity, which is particularly advantageous when, for example, the patient is non-responsive or is unable to actively take part in the identification for other reasons. The identification can furthermore ensue utilizing RFID chips, in particular RFID tags, or NFC chips or gesture recognition.

Identification can in particular occur by direct on-site accessing or by remote accessing of one of the treatment carts or user interfaces which can in particular be allocated to the treatment cart.

Preferably, the control system is designed to implement the patient or user identification procedure when a predetermined identification criterion exists. One such identification criterion can in particular be a patient or user request for identification, for instance by activating a user interface. Such an identification criterion can also be the presence of a user or a patient in the vicinity of a treatment cart or a user interface—in particular in the same room or at a distance of at most 5 m, preferably at most 1.5 m, and further preferentially no more than 0.5 m.

Identification can require the prior system registration of the patient or user so that the system has comparative data for the identification stored on the data storage apparatus for identification data, thus in particular identification data characterizing the patient or user. In particular, the control system can be designed to register a patient or a user into the system, whereby a uniquely allocatable set of patient data is allocated to the patient or, in the case of a user, a uniquely allocatable set of user data is allocated to the user which contains the patient identifier characterizing the patient or, respectively, the user identifier characterizing the user. This patient data set/user data set can be stored in the data storage apparatus for identification data.

Preferably, identification data of patients or users is captured in the identification procedure by means of a sensor device for identification data and this recorded identification data compared to data of the data storage apparatus for identification data. Preferably, the sensor device for identification data is configured as a biometric reader, in particular an iris scanner, fingerprint scanner or camera for facial or gesture recognition. In particular, at least one of the user interfaces can comprise such a sensor device for identification data. Alternatively or additionally, one of the user interfaces can be designed for one or more inputs from a user or patient by means of which a user or patient can be identified. To that end, a user interface of such configuration can in particular comprise or consist of an identifier reader unit, for instance preferably a bar code reader, an RFID reader, a document reader or a magnetic strip reader, whereby the inputs can be scanned by such reader devices for the identification. A user interface of such configuration can also comprise a keyboard, a mouse or a touch-sensitive screen for inputting text and/or graphic symbols, for instance a login text and a password text, a secret code or a recognition gesture.

According to one preferential further development, the control system is designed to log the user into the system as a function of successful system identification, determine a user identifier, execute the selection process and/or limit the release of medical accessories to accessory types for which the registered user is authorized and/or, if the user is not successfully identified, not execute the selection process and/or limit the selection or release of medical accessories to accessory types for non-authorized users. This thereby advantageously enables increasing safety. According to one preferential variant, the control system is designed to personalize the registered user and in particular designed to adapt outputs at one of the user interfaces and/or the selection method to the registered user, whereby this in particular enables increasing user convenience, operational efficiency, treatment safety and/or treatment quality. In particular the determining of the accessory set parameters can thereby be adapted to the registered user such that in the case of multiple possible compilations of medical accessories for the treatment to be performed—thus in particular when at least two different accessory sets are suitable for the treatment to be performed—an accessory parameter is determined for the medical accessories preferred by the registered user. Such a preference can be stored in particular in the accessory database, preferably as a respective particularly treatment-specific allocation between a preference value and a respective user.

According to one preferential further development, one of the user interfaces is designed for one or more inputs from the, in particular registered, user, by means of which a patient to be treated is determined and on the basis of which the control system determines a patient identifier associated with the patient to be treated as a result of said inputs. Additionally or alternatively, the patient can also be determined by means of identification and the control system determines the patient identifier of the identified patient to be treated based thereon. In particular, the patient can be also a user. Furthermore, the selection method further comprises the method step of determining the patient identifier of the patient to be treated. In addition, in the method step of determining the accessory set parameter of the selection method, the accessory set parameter is determined on the basis of the treatment identifier and/or the patient identifier. Determination of the patient to be treated can advantageously enable in particular a personalization. One advantage of determining the accessory set parameter on the basis of the patient identifier can in particular lie in being able to select those medical accessories from among the plurality of medical accessories which are particularly suitable for the patient to be treated—the selection thus personalized. Preferably, when multiple compilations of medical accessories are possible for the treatment to be performed when determining the accessory set parameter—thus in particular at least two different accessory sets are suitable for the treatment to be performed—the accessory set parameter is determined for those medical accessories which are characterized by the patient identifier as being particularly suitable and/or preferred for the patient to be treated. Such suitability can in particular be stored in the accessory database or in a patient database, whereby the database preferably assigns a suitability value, in particular in treatment-specific manner, to a medical accessory in respect of a patient or patient identifier.

According to one preferential further development, the control system can be designed to determine the treatment identifier of the treatment to be performed on the basis of a patient identifier of the patient to be treated or only allow those treatments from among a plurality of possible treatments during the determining of the treatment to be performed for said patient which are associated with the patient to be treated by means of his patient identifier. This advantageously enables increasing the treatment safety, the treatment quality and/or the operational efficiency.

According to one preferential further development, the control system comprises a treatment database which is configured for data sets on a plurality of treatments and stored on a data storage apparatus of the control system. In particular, such a data set can be allocated to a specific treatment and, to that end, preferably comprises a treatment identifier of said treatment. Such a data set can also comprise treatment data. Such a data set which is associated with a specific treatment having multiple treatment steps can also comprise data in respect of one or more treatment steps of said treatment. Each treatment step can thereby in particular be characterized by a treatment step identifier and the data set comprise one or more treatment step identifiers.

Furthermore, such a data set can comprise data on a medical accessory as pertains to a specific treatment or pertains to a specific treatment step. In particular, such data can relate to a medical accessory: information on the appearance of the medical accessory; information on whether the medical accessory is used in the specific treatment or specific treatment step; the order of the medical accessory in the treatment or treatment step; and/or movement trajectories which correspond to the medical accessory's movements during the treatment or treatment step.

Furthermore, such a data set can comprise data on an area of the patient's body which is affected, and particularly changed, by a specific treatment or a specific treatment step. In particular, such body area data can relate to: information on the appearance of an area of skin, information on whether the body area is affected by the specific treatment or the specific treatment step; a change in the body area due to the specific treatment or the specific treatment step—preferably a change to the color of the body area, in particular the skin—and/or movement trajectories which correspond to the body area's movements during the treatment or treatment step.

According to one preferential further development, the mobile selection system further comprises a detection system for treatments. The detection system for treatments detects an individual involved in the treatment, in particular the patient, a medical accessory, in particular a medical accessory of the accessory set or a medical accessory for a treatment, and/or their arrangement and/or movement relative to each other by means of sensor technology-based measurement of radiation, in particular light, ultrasound, weight and/or inertia. Based on that, the detection system for treatments determines, preferably employing the accessory database and/or the treatment database, the treatment performed and/or a treatment step performed, in particular in respect of the performed treatment.

Preferably, the detection system for treatments is configured as a treatment cart module or a treatment cart module comprises one more components of the detection system, in particular its sensor system.

Preferably, the mobile selection system, in particular the treatment cart, has a disposal apparatus for medical accessories which comprises such a treatment detection system.

According to one preferential further development, a disposal apparatus for medical accessories comprises a treatment detection system which is designed to detect medical accessories to be disposed of by said disposal apparatus. Preferably, the disposal apparatus for medical accessories has a disposal bin with a disposal opening, whereby the sensor system of the detection system is configured and in particular disposed so as to identify a medical accessory transported through the disposal opening into the disposal bin for disposal—in particular by means of optical or weight detection.

Preferably, the detection system is designed to determine the treatment performed by means of the treatment database and/or the accessory database on the basis of one or more medical accessories detected by way of the disposal. Alternatively, the treatment performed can also preferably be determined, and particularly its treatment identifier established, by user inputs.

The detection system is additionally preferably designed to determine the treatment step performed by means of the treatment database and/or the accessory database on the basis of one or more medical accessories detected by way of the disposal as well as preferably on the basis of the treatment identifier. In particular, the treatment identifier enables minimizing the search area for possible treatment steps, whereby in particular the treatment step determination can be realized in simplified and/or more robust manner; i.e. in particular less prone to errors.

It is further preferential for the detection system to be designed on the basis of one, in particular treatment-specific or accessory-specific, success criterion and whether the treatment step was successfully performed determined on the basis of the detected disposed-of medical accessories. Thus, in particular a torn disposable glove can correspond to an unsuccessful attempt of putting on the disposable glove. A bent needle or a catheter or infusion tube not filled with fluid can in particular also correspond to the unsuccessful use of same. The interval of time between the releasing of the medical accessory and its disposal can also be a success criterion. Thus, in particular a section of adhesive tape which is disposed of no more than 30 seconds after its release, preferably at the most 5 seconds, corresponds to an unsuccessful use—particularly an attempt which failed to stick to the skin or an unsuccessful fixing of a catheter or cannula using said adhesive tape section.

Preferably, the disposal apparatus is configured as a treatment cart module or a treatment cart module comprises or consists of one or more components of the disposal apparatus, in particular the disposal bin and/or the sensor system of the detection system.

According to one preferential further development, the control system is designed to perform an assist process. The assist process comprises at least the procedural step of determining one or more assistance parameters characterizing the treatment to be performed, a treatment step to be performed of the treatment to be performed and/or a medical accessory for same. Preferably, the control system determines the treatment to be performed and/or the treatment step to be performed by means of the treatment detection system. Preferentially, and alternatively or additionally, the control system determines the treatment to be performed and/or the treatment step to be performed on the basis of user input specifying the treatment to be performed and/or the treatment step to be performed. One advantage of the assistance parameter can be in particular lie in being able to implement and/or realize an assist function on the basis of same which supports in particular the user or the patient in the treatment and thus can increase the operational efficiency, treatment safety, treatment quality, user convenience and/or patient satisfaction.

According to one preferential variant, the mobile selection system, in particular the control system, comprises a data storage apparatus for assistance information and/or the treatment database is designed for data sets having assistance information relative to a treatment or treatment step. In addition, one of the user interfaces is designed to output assistance information and/or the mobile selection system, in particular one of the treatment carts, comprises an additional user interface for assistance information. Moreover, the assist process further comprises a procedural step in which, based on the assistance parameter, assistance information corresponding to the assistance parameters is read from the storage apparatus for assistance information or from the treatment database respectively as well as a procedural step in which the control system outputs the assistance information via the user interface for assistance information.

As defined by the invention, "assistance information" can in particular be acoustic or visual instructions on the treatment to be performed, the steps of a treatment and/or their sequence, the respective treatment step to be performed and/or the medical accessories. Such assistance information can also be instructions on how the treatment or the treatment step is to be respectively performed in each case and/or how a specific medical accessory is to be used in particular for the treatment or the treatment step. Such assistance information can also be information on the patient to be treated. Such patient information can in particular be information on patient characteristics and/or be coded as patient data. For instance, in the case of dialysis patients, the presence of an arteriovenous fistula or a prosthetic shunt and/or the last puncture sites used for vascular access and/or recommended injection sites can preferably be stored; and the assist functions can moreover be information/instructions on where and/or how the vascular access to the patient's blood for dialysis is to be made, in particular at which location a cannula is to be inserted and/or a catheter placed.

Preferably, the mobile selection system, in particular the control system, comprises a patient database for the patient information and a data storage apparatus for same.

One advantage of outputting specific assistance information—thus in particular the assist function—can in particular be that of thereby supporting an individual involved in the treatment, whereby errors can in particular be avoided, the treatment quality being able to be increased and/or enabling the patient—as an individual involved in the treatment and guided by the assistance information—to be able to perform the treatment or treatment step himself. Such active patient participation enables in particular patient satisfaction to be increased and/or frees up personnel.

According to one preferential variant, the control system is designed to control the at least one release mechanism at least on the basis of the accessory set parameter and the assistance parameter so as to release those medical accessories of the accessory set required for the treatment step to be performed and/or which are to be used after the medical accessory currently being used. Preferentially and alternatively or additionally, the at least one release mechanism is designed to release the medical accessories as a function of the assistance parameter. Preferentially and alternatively or additionally, the at least one release mechanism is designed to display, pursuant to the control of the control system and/or on the basis of the assistance parameter, those storage areas in which the medical accessories of the accessory set necessary for the treatment step to be performed and/or which are to be used after the medical accessory currently being used are stored. One advantage of the, in particular automated, release on the basis of the assistance parameter—thus in particular assist function—can in particular lie in the releasing of the necessary medical accessories dependent on the treatment's progress, whereby in particular mix-ups and/or work steps involved in extracting or locating medical accessories can be avoided. In addition, displaying the storage areas can facilitate the locating of medical accessories or, respectively, storage areas containing the necessary medical accessories.

According to one preferential variant having a disposal apparatus for medical accessories, the disposal apparatus comprises a lockable disposal opening and a locking mechanism for the disposal opening. The control system is thereby designed to control the locking mechanism such that it opens the disposal opening as a function of the assistance parameter, in particular for specific treatment steps, and/or locks it as a function of the assistance parameter, in particular after the treatment or for transport. The assist function here is in particular the automated opening and/or closing of the disposal opening. This thereby advantageously enables an increase in the convenience of use and/or the safety.

According to one preferential further development, the mobile selection system, in particular one of the treatment carts, comprises a recording apparatus having an image sensor device which is designed to capture one or more images, in particular an image sequence or a video film, before, after or during the treatment via the image sensor device and log same by means of a data storage apparatus for image recordings and/or transmit same for storage by means of data connection to the control system. This advantageously enables the treatment to be monitored and/or subsequently reconstructed, for instance for evaluation or quality improvement. In addition, a patient who performs the treatment or steps thereof in particular at home, where medical personnel is not present at the patient's location during the treatment, can be monitored and supported, preferably via a communication connection in the opposite direction. According to one preferential variant, the recording apparatus is designed as a treatment cart module or a treatment cart module comprises one or more components of the recording apparatus, in particular the image sensor device. In particular, such an image sensor device can be a camera module.

According to one preferential further development, the mobile selection system, in particular one of the treatment carts, comprises an inventory monitoring system for the treatment carts and/or for the one of the treatment carts. The inventory monitoring system is designed to determine, for at least one of the storage areas, the number of stocked medical accessories of the accessory type stored therein. In addition, the control system is designed to perform an inventory determination analysis comprising the method step of determining an actual inventory of stocked medical accessories of the plurality of medical accessories by means of the inventory monitoring system, in particular at least in respect of the at least one storage area.

Preferably, data related to the medical accessories stored in the storage area is acquired by means of a sensor system which is based on measurement of radiation, in particular light and/or weight, of the inventory monitoring system and, based thereon, the number determined. Preferentially and additionally or alternatively, the number is determined by counting the current consumption of the medical accessories of said accessory type—i.e. in particular reducing the number starting from an initial value by the respective number of medical accessories of said accessory type released during the releasing process.

Preferably the inventory monitoring system is designed to determine the number of stocked medical accessories for at least all the storage areas for which a release mechanism is designed to release medical accessories from same and the control system is designed to determine the actual inventory at least in respect of said storage areas.

One advantage of determining the actual inventory by means of the inventory monitoring system can in particular be being able to adapt the selection and release of medical accessories to the actual inventory, whereby in particular the treatment safety, efficiency and/or treatment quality can be increased and/or—particularly compared to manually determining the actual inventory—personnel workload and/or sources of error reduced.

According to one preferential further development, one of the storage devices is designed to be equipped with an accessory holder which comprises one or more storage areas each equipped with medical accessories of a respective accessory type; i.e. in particular accommodate said accessory holder in a positive fit. This advantageously enables the inventory of medical accessories in the storage device to be stocked or replenished by equipping the accessory holder and thus in particular prevents needing to individually arrange the medical accessories of the accessory types in the storage areas. In particular, the accessory holder can thereby be equipped by a pick-and-place system, in particular the mobile selection system.

The invention further relates to a method for equipping a treatment cart comprising the following method steps: —Determining a target value with respect to the number of medical accessories of an accessory type and an actual value with respect to the actual inventory of said medical accessories in the treatment cart, in particular in a storage area of a storage device of the treatment cart; —If the actual value is lower than the target value, emitting an accessory shortage signal identifying a shortage of medical accessories of said accessory type.

Preferably, the signal is output to a user interface and a user of the treatment cart is thereby advantageously supported in the equipping of the treatment cart. Preferably, assistance information with instructions in respect of the medical accessories to be equipped, their supply in an external storage and/or the storage area for said equipped medical accessories is thereby additionally output.

Preferentially and alternatively or additionally, the signal is output via a data connection to a pick-and-place system. Said pick-and-place system is thereby configured to equip an accessory holder on the basis of the signal and/or to equip the treatment cart, provided it is arranged adjacent to the pick-and-place system, with the medical accessories for which the shortage of its accessory types was signaled. Preferably, the treatment cart can be equipped with the accessory holder for this purpose.

A second aspect of the invention relates to a treatment cart for a mobile selection system in accordance with the first aspect of the invention. The treatment cart comprises one or more storage devices, wherein the storage devices have at least two storage areas for medical accessories each of a respective accessory type and at least one release mechanism for releasing medical accessories.

The previously cited possible advantages as well as embodiments, further developments or variants of the first aspect of the invention also apply correspondingly to the inventive treatment cart. Inversely, the following cited possible advantages as well as embodiments, further developments or variants of a treatment cart according to an embodiment of the second aspect of the invention also apply correspondingly to a mobile selection system according to an embodiment of the first aspect of the invention having such a treatment cart.

According to one preferential further development, the treatment cart exhibits one of the user interfaces of the mobile selection system; i.e. in particular the treatment cart comprises a user interface which is configured in correspondence with a user interface of the first aspect of the invention—preferably for inputs for specifying a treatment to be performed. In addition, the treatment cart comprises a drive apparatus having at least a part of the control system of the mobile selection system and/or a communication device for forming a data connection to the control system or another part of the control system respectively. The drive apparatus for the control of the at least one release mechanism is thereby equipped by the control system to electrically actuate the at least one release mechanism on the basis of the accessory set parameter. To that end, the treatment cart preferably comprises a bus system and the drive apparatus is designed to establish a data connection to the at least one release mechanism via said bus system and/or comprises a data connection to the at least one release mechanism via the bus system. In particular, the user interface and the drive apparatus are mechanically connected or connectable to the treatment cart so as to be able to be transported together with the other components of the treatment cart. Preferably, the user interface and/or drive apparatus are designed as a treatment cart module.

Doing so enables the treatment cart to be advantageously operated by means of the user interface of the treatment cart, in particular without a treatment cart needing an external user interface.

One advantage of the treatment cart having a drive apparatus can in particular be that of the control, emanating from the control system, being able to ensue electrically in the treatment cart by means of the drive apparatus; i.e. in particular by means of electrical signals, whereby in particular the electrical control, preferably by means of electrical signal lines, for instance as a component part of a bus system, can be realized in a more technically robust and/or more economical manner compared to a mechanical control.

One advantage of a preferential variant in which the treatment cart does not comprise the control system or at least components thereof and/or is not mechanically connected to same respectively, can in particular lie in the control system or component parts thereof being able to be disposed at a different location than the treatment cart and the treatment cart being able to be controlled from there and/or without mechanical connection. This advantageously enables reducing in particular the weight of the treatment cart, lowering the manufacturing costs and/or disposing expensive or sensitive components of the control system at a location which is particularly suitable for same—for instance a control room or a server room. Moreover, such a control system can be designed to control multiple treatment carts via its respective drive apparatus.

According to one preferential variant, the drive apparatus can also implement parts of the control, in particular a regulating of the at least one release mechanism, and comprise at least one control loop to that end. This advantageously enables the drive apparatus to adapt the control to said treatment cart and/or enables quick feedback during control, in particular regulation, particularly compared to a control system arranged at another location implementing the control and in particular the regulation.

One advantage of a preferential variant in which the drive apparatus comprises the entire control system can be in particular be that such a treatment cart can be operated independently of further components of a mobile selection system. In such a variant, the drive apparatus, or control system respectively, of the treatment cart can also be designed to control at least one further treatment cart.

According to one preferential further development, the treatment cart comprises an energy storage for supplying energy to the treatment cart. Preferably, the energy storage comprises or consists of an independent power source, in particular a rechargeable battery, for supplying the treatment cart with electrical energy. The treatment cart is thereby advantageously independent of an external power supply, at least periodically until the energy storage is depleted. Such a treatment cart with its own energy storage can also be used at locations which do not allow for an external power supply and/or can be operated at the respective location without being installed; i.e. in particular connected to an external power supply.

According to one preferential further development, the treatment cart comprises a connecting device for connecting to an external power supply, by means of which the treatment cart is supplied with energy. Preferably, the connecting device comprises or consists of a plug for an electrical outlet of a power supply system and, in particular, a power cable. This advantageously enables external energy to be provided to operate the treatment cart, whereby in particular costs can be reduced and/or operational life extended since particularly a preferably additionally provided individual energy storage of the treatment cart does not become depleted, and is further preferentially charged, while the external power is being supplied.

A third aspect of the invention relates to a method for the selection of medical accessories from among a plurality of medical accessories, in particular for a cannulation of patient blood vessels and/or for a dialysis treatment. One part of the method for selecting medical accessories is thereby a method for releasing said medical accessories from a treatment cart having multiple storage devices. The medical accessories of the plurality of medical accessories are thereby stored in at least two storage areas of the storage devices sorted according to their respective accessory types. The inventive method comprises the following method steps. In one method step, a user interface which is data-linked to a control system acquires one or more inputs from a user, by means of which a treatment to be performed is defined. In a further method step, the control system determines a treatment identifier of the treatment to be performed on the basis of said inputs In a further method step, the control system determines one or more accessory set parameters characterizing a medical accessory from among one or more of the medical accessories suitable for the treatment to be performed on the basis of an accessory database and at least on the basis of the treatment identifier of the treatment to be performed, wherein the accessory database comprises data sets on the plurality of medical accessories and is stored on a data storage apparatus of the control system. In a further method step, in particular the releasing process, a release mechanism which is designed to release medical accessories from at least one of the storage devices and which is data-linked to the control system is controlled on the basis of the accessory set parameters. In a further method step, in particular the releasing process, the release mechanism releases those medical accessories for which the at least one of the storage devices exhibits storage area for their accessory types and which are characterized by the accessory set parameters on which the control of the release mechanism is based.

The previously cited possible advantages as well as embodiments, further developments or variants of the first and/or second aspect of the invention also apply correspondingly to the inventive method for selecting medical accessories.

In the sense of the invention, a "medical accessory"—or "accessory" for short—is a device, an instrument, a material, a substance or a combination thereof which is predetermined and/or applicable to the treatment of a patient. In particular, a medical accessory can be consumed in intended use. Alternatively, a medical accessory does not have to be consumed in intended use; i.e. is used in multiple treatments of one or more patients.

In particular, a medical accessory can be a medicinal product usually having at least substantially pharmacological, metabolic or immunological effect in intended use. Preferentially, such a medicinal product is of a pharmaceutical form, preferably for instance capsules, pills, tablets, pastes, ointments, injection doses or drug solutions in a predetermined dosage, dosing device, administering device and/or storage device for the treatment, preferably for instance capsules or tablets in a blister pack, syringes with single or multiple doses of an injectable drug, medical syrups in bottles with or without dosage measuring cups or pharmaceutical preparations in a spray bottle having a spraying system.

In particular, a medical accessory can be also a medicinal product usually having at least substantially somatic, physical or physicochemical effect in intended use or by means of which a pharmaceutical is administered. Such medicinal products are in particular surgical instruments such as surgical hooks, retractors, spreaders, scalpels, scissors or forceps. Such medicinal products are in particular also needles, syringes, cannulas, Seldinger wires or catheters.

Protective gear for patients or individuals participating in the treatment can also be a medical accessory in the sense of the invention. Such protective gear in particular includes gloves to protect against chemicals or infection, preferably disposable gloves for instance made of latex, nitrile rubber or vinyl, medical mouthguards, medical hair nets or protective glasses. In particular, disinfectants, dressing materials or cosmetic products can also be medical accessories in the sense of the invention.

A medical accessory in the sense of the invention constitutes in particular a device, an instrument, a material, a substance or a combination thereof for patient cannulation, preferably for instance for a dialysis treatment. This in particular includes syringes, cannulas, infusion tubes, disposable gloves, disinfectants, swabs, dressing material, bandages, tapes and adhesive strips.

In addition, a medical accessory in the sense of the invention has physical dimensions and a weight which enables an individual participating in the treatment to transport and/or handle the medical accessory. Thus, the weight of such a medical accessory is in particular no more than 10 kg, preferably no more than 1 kg, preferably no more than 300 g, preferably no more than 100 g and further preferentially at the most 30 g. The physical dimensions to such a medical accessory are in particular of a length of no more than 1.5 m, preferably no more than 1 m, preferably no more than 0.5 m, preferably no more than 30 cm, preferably no more than 15 cm and further preferentially at the most 5 cm, wherein the same applies to the width and height. It is thereby needless to say that particularly the physical dimensions of such a medical accessory, such as an infusion tube or a tape, can also vary upon being unrolled, rolled or sectioned, whereby relevant to the handling or transport is that the physical dimensions of such a medical accessory are variable to the extent of exhibiting no more than the length, width and depth indicated above.

Preferably, the medical accessory in the sense of the invention can be designed and in particular configured such that a treatment apparatus for treating a patient can utilize the medical accessory in the treatment; in particular accommodate, operate, manipulate and/or administer.

As defined by the invention, a "medical accessory set"—or "accessory set" for short—is an assemblage of one or preferably a plurality of medical accessories. Preferably, a medical accessory set is provided for a specific treatment and/or a specific patient and comprises thereto at least one medical accessory required, particularly suitable and/or selected for said patient and/or said treatment.

In the sense of the invention, a "medical accessory holder"—or "accessory holder" for short—is to be understood as at least one apparatus for supporting and/or suspending a medical accessory set.

Preferably, the accessory holder can comprise one, preferably at least two, further preferably all of the medical accessories of the accessory set, thus in particular be fitted with said medical accessories. In particular, the accessory holder can be pre-equipped with at least part of an accessory set so as to already comprise at least said part of the accessory set. Doing so enables providing accessory holders with specific, in particularly frequently needed, accessory sets, in particular without their needing to be individually fitted to a respective requirement or selection. It can also be provided for such an accessory holder to be equipped with a further part of an accessory set, whereby such an accessory holder can be equipped, in particular completely, with different medical accessory sets, whereby the accessory holder is on the one hand individually equipped with the respectively specific accessories of the accessory set while, on the other hand, that part of the accessory set or group of medical accessory sets which is common to same and/or frequently needed does not need to be individually equipped to a specific requirement or selection.

It is also preferable for the accessory holder to comprise one, preferably at least two, further preferably all of the medical accessories for the equipping of a storage device of a treatment cart, thus in particular be fitted with said medical accessories. This advantageously enables the inventory of the storage device's medical accessories to be filled or respectively replenished by equipping the storage device with said equipped accessory holder.

In particular, an accessory holder can comprise a receiving device designed to accommodate one, preferably at least two and further preferably all of the medical accessories of the accessory set, in particular detachably connect to same in form-fit, force-fit or materially bonded manner and/or enclose same and/or wherein the medical accessories are thus arranged in the receiving device. Preferably, an accessory holder comprises one or more retention devices for respectively receiving a medical accessory of the accessory set. In particular, medical accessories for a specific treatment can thereby be specifically arranged, preferably on the basis of their order of use in the specific treatment.

In particular, the accessory holder can be configured as a medical accessory container, wherein same or the receiving device of the accessory holder comprises or consists of a container which accommodates, thus in particular spatially encloses, one, preferably at least two, and further preferably all of the medical accessories. Such an accessory container is preferably of box-shaped design and is in particular referred to as an accessory box.

Preferably, an accessory holder is configured and in particular formed such that a treatment apparatus for the treatment for which the accessory holder is intended or an individual participating in the treatment can utilize the accessory holder, thus in particular hold, open, operate, manipulate, release and/or remove the medical accessories of the accessory set with which the accessory holder is equipped.

In particular, an accessory holder itself, particularly an equipped accessory holder, can be a medical accessory which in particular consolidates the medical accessories with which the accessory holder is equipped, able to be provided for a treatment and/or provide its functions.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

A "group of treatments" in the sense of the invention can be respective specific operations, therapy for a specific illness, the initial examination of a patient, or a dialysis treatment which in turn can comprise sub-groups, in particular hemodialysis, hemofil-tration, hemodiafiltration, hemoperfusion or peritoneal dialysis treatments.

As defined by the invention, an "individual involved in the treatment" can in particular be understood as an attending person, for instance a physician, or an individual providing treatment support, for instance a nurse. In particular, the patient to be treated can himself also be an individual involved in the treatment or an attending person.

As defined by the invention, a "group of patients" can in particular be either male or female patients, patients with a specific chronic illness, patients having a certain blood type, patients having a certain skin type, dialysis patients with an arteriovenous fistula (AV fistula)—i.e. with a Cimino shunt—, dialysis patients with a vascular graft access (AV graft)—i.e. in particular with a Scribner shunt—or dialysis patients who require a central venous catheter line.

As defined by the invention, a "treatment apparatus" is to at least be understood as an apparatus which is equipped to perform and/or support one or more patient treatments. A treatment apparatus is in particular a surgical robot, a cannulation apparatus—in particular for a vascular access and/or in particular a cannulation robot—, a dialysis apparatus or a disinfecting apparatus for disinfecting an area of a patient's body.

In the sense of the invention, a "storage device" is a device for storing objects, in particular devices, instruments, materials or substances, in particular of medical accessories or accessory holders. The storage device can thereby preferably accommodate the objects to be stored, or at least a part thereof; i.e. in particular spatially enclose or at least partly surround them, particularly in conjunction with an apparatus comprising one of the storage devices.

Preferably the storage device, in particular working in conjunction with the apparatus comprising the storage device, exhibits at least one storage device section having an interior area, wherein the storage device section spatially and physically separates the interior area from the surrounding area of the storage device in a closed state. In particular, the objects to be stored can be arranged in the interior area, and thereby stored, and the interior area spatially and physically accessible from the area surrounding the storage device in an open state.

Preferably, the storage device comprises at least two storage areas spatially separated from one another. This enables different objects to be stored spatially separated from each other by the at least two storage areas and, in particular, be addressed based on the storage area. Preferably, such a storage area is designed as an interior area.

Preferably, the storage device comprises a climate control device for controlling—and in particular regulating—the storage conditions; i.e. in particular controlling or regulating the atmospheric humidity and/or temperature. Further storage conditions are in particular a medium in the storage device, or in the interior areas of the storage device respectively, preferably for instance air, an inert gas, a storage liquid or bulk material for storage—such as anti-vibration polystyrene balls—, the presence and/or absence of certain chemicals such as acids or alkalis as well as the effects of radiation such as visible light, ultraviolet light, infrared light, radioactive radiation or verberation. Preferably, the storage conditions for the interior areas of the storage device can be separately controlled and/or regulated.

In the sense of the invention, a "database" is an electronic data management system comprising in particular a database and a program code for administering the database; i.e. in particular for storing, reading, querying, modifying and/or deleting data of the database, in particular the data sets.

Preferably, a data processing apparatus is designed to load the program code from a data storage apparatus for the database, run same as well as load at least a part of the database from a data storage apparatus for the database, and save the database as needed after a modification. In particular, to query the accessory database, information, in particular electronically or optically coded information, can be sent to the data processing apparatus, whereupon that part of the database, or data set respectively, which corresponds to the transmitted information is output via the program code. In particular, the data sets can thereby be retrieved and thus read (or with a data-changing query, also modified), with a data field of the respective data set having a specific value or being in a specific value range. Preferably, the database is configured as a relational database, in particular as an SQL database.

In the sense of the invention, an "accessory database" is a database for medical accessories The accessory database, in particular the database, is designed to hold data sets on medical accessories. In particular, at least one data set in each case characterizes a medical accessory and/or its properties. Preferably, each of the medical accessories recorded in the accessory database is thereby assigned an accessory identifier and the accessory identifier stored in the data sets relating to the respective accessory as information able to be electronically retrieved and in particular queried. Also preferably, the properties of the accessories are correspondingly stored in at least one of the data sets on the respective accessory as information able to be electronically retrieved and in particular queried.

Correspondingly, a "patient database" in the sense of the invention is a database of patients. The patient database, in particular its database, is designed to comprise data sets on patients. In particular, at least one data set in each case characterizes a patient and/or his characteristics. Preferably, each of the patients recorded in the patient database is thereby assigned a patient identifier and the patient identifier stored in the data sets relating to the respective patient as information able to be electronically retrieved and in particular queried. Also preferably, the characteristics of the patient are correspondingly stored in at least one of the data sets on the respective patient as information able to be electronically retrieved and in particular queried. Preferably at least one characteristic relates to the suitability of a medical accessory for the treating of the patient. Also preferably at least one patient characteristic relates to the gender of the patient, an acute or chronic illness of the patient, allergies of the patient, his age, name, blood type, skin type and/or the treatments to be performed. Also preferably at least one patient characteristic relates to, particularly in the case of a dialysis patient, the vascular access options to the blood circulation, in particular the presence— and preferably the specifics—of an arteriovenous fistula or a prosthetic shunt, and/or the last puncture sites used for vascular access and/or recommended puncture sites.

Correspondingly, a "treatment database" in the sense of the invention is a database of treatments which are preferably each characterized by a treatment identifier. Preferably, such a treatment database, in particular its database, is designed to hold data sets on treatments and/or on one or more treatment steps of at least one treatment. The treatment steps are thereby preferably each characterized by a treatment step identifier.

As defined by the invention, an "identifier" is an item of information which characterizes something, in particular an object, a procedure, a method, a characteristic or a person, and which can be processed by a data processing apparatus, thus in particular a signal sequence and/or its mechanical, electrical or optical representation in a data storage. The information thereby preferably comprises a portion which characterizes the information as an identifier of a specific type—in particular compared to further identifiers of other types. An identifier is in particular information on a unique number, a unique designation and/or name, provided same is unique or can be made unique by way of an additional identifier.

A "treatment identifier" in the sense of the invention is an identification which characterizes a specific treatment or a specific group of treatments. In particular, the specific treatment or group of treatments to which a specific treatment is assigned can be identified by means of the treatment identifier. A treatment identifier is in particular information on a treatment number, a unique designation for a treatment or a group of treatments or a unique treatment name or treatment name made unique. The information thereby preferably comprises a portion which characterizes the information as an identifier of a treatment or group of treatments respectively—in particular compared to other identifiers not related to a treatment or a group of treatments respectively.

Correspondingly, a "treatment step identifier" in the sense of the invention is an identifier characterizing a specific step of a treatment.

Correspondingly, a "patient identifier" in the sense of the invention is an identifier which characterizes a specific patient or a specific group of patients. Such a patient identifier can in particular be information on a patient number, a (health) insurance number, a patient name or a patient ID number. Preferably, this information is stored on a patient card, an electronic data storage and/or on a document for the patient, in particular as a bar code, magnetic strip, RFID tag or an alphanumeric representation.

Correspondingly, a "user identifier" in the sense of the invention is an identifier characterizing a specific user or a specific group of users.

Correspondingly, an "accessory identifier" in the sense of the invention is an identifier which characterizes a specific medical accessory. A representation of the information of said accessory identifier can in particular be stored on or by means of a packaging of the medical accessory, for instance as a bar code or RFID tag.

Correspondingly, a "treatment cart identifier" in the sense of the invention is an identifier which characterizes a specific treatment cart. Preferably, the treatment cart comprises in particular an electronic data storage—preferably for instance a magnetic strip, an RFID tag, a bar code or an alphanumeric representation—in which its treatment cart identifier is stored in a readable format. Preferably, the data storage is integrally connected to the treatment cart, thus in particular an RFID tag is affixed to the treatment cart or a bar code or alphanumeric representation respectively engraved or imprinted on the treatment cart.

Correspondingly, a "treatment cart module identifier" in the sense of the invention is an identifier characterizing a specific treatment cart module.

Correspondingly, a "user interface identifier" in the sense of the invention is an identifier which identifies a specific user interface.

A bar code can also be a two-dimensional bar code; i.e. a so-called "2D code."

As defined by the invention, a "control system" is a system which comprises a data processing apparatus and/or a volatile or non-volatile data storage, in particular a data storage apparatus, and is designed to control a system having the control system, in particular the mobile selection system, the component parts of same and/or one or more apparatus external of the system; i.e. in particular also other systems or mechanisms, preferably for instance an external treatment cart or a pick-and-place system. The control system is preferably configured to implement the selection method and/or the assist function in particular by a program code applicably designed for this purpose and executable by a data processor.

The control system can be formed by a single control apparatus. Preferably, the control system comprises a plurality of control devices which can be independent devices or components of other system apparatus, in particular one of the user interfaces and/or one of the treatment carts. In particular, some or all of these control devices can be structured into a data exchange network. In the case of the at least one user interface device comprising its own control device and/or one of the treatment carts comprising its own control device, these control devices can be regarded as component parts of the control system. It is however also possible for the control system to not comprise these optionally provided control devices.

In particular, a treatment cart can comprise a control apparatus as its own control device. Preferential and alternatively or additionally, the drive apparatus itself is a control system, comprises the control system or comprises components of the control system, in particular a control device.

The control system of the system and/or the treatment cart or respectively one of the treatment carts and/or the drive apparatus and/or the user interface or respectively one of the user interfaces—in particular all—can be integrated into one physical device unit, although each can also be their own physical device unit. A physical device unit can in particular be a module, in particular a treatment cart module, which is at least or can be data-linked to the control system.

The control system and/or one of the user interfaces and/or the drive apparatus or component parts of said components can also be at least partly implemented by software functions or can, in particular, partly implement program code. A treatment cart can comprise a drive apparatus which, in combination with software functions, at least partially implements in each case one or more functions of the control system and/or the treatment cart. Correspondingly, a user interface can comprise a control device which, in combination with software functions, at least partially implements in each case one or more functions of the mobile selection system and/or the control system and/or the treatment cart.

In the sense of the invention, "control," in particular control provided by a control system, preferably ensues on the basis of an identifier, an input variable, one or more parameters or a combination thereof. The control can also include regulation. Thus, a control system can for instance control a release mechanism for a storage device designed as a drawer on the basis of accessory set parameters such that the release mechanism extends out the drawer to a specific storage area of the drawer, whereby the drawing out to the extended distance is regularly detected and the control system also controls the release mechanism by means of a control loop, in addition to the accessory set parameters, with regard to the respectively covered distance.

As defined by the invention, "configured" refers to an apparatus not only being in principle suited to fulfill a specific function—for instance only after a specific program code has been loaded; i.e. the apparatus programmed, or the apparatus formed in a specific way—, but the apparatus already possesses all the means necessary in order to actually fulfill the function. Preferably, the apparatus is to that end already programmed with a program code for said function and/or already configured and/or arranged and/or exhibits such a configuration thereto that the apparatus actually fulfills the function.

As defined by the invention, "on the basis of" is at least to be understood as "due to" and/or "as a function of." In particular, the one or more parameters to be determined can be determined on the basis of an identifier, an input variable or one or more of the preceding parameters or a combination thereof. The result, i.e. the specific parameters, can thereby depend on part of the basis on which the determination is based—in particular functional, particularly linear or polynomial—while not depending on another part of the basis. The dependency can also be contingent on a part of the basis; i.e. in particular the part of the basis determining on which parts of the basis the result depends. The same applies accordingly to the control or actuation, in particular based on parameters, identifiers or input variables.

To be understood by a "data processing apparatus" in the sense of the invention is at least one apparatus configured to process data; i.e. in particular to receive data, store received data, read out stored data, transform received and/or stored and/or read data by means of logical and/or mathematical operations, store transformed data, and/or output transformed and/or read data. Preferably, such a data processing apparatus is programmable; i.e. a program code in particular at least partially specifies the method for processing the data and at least part of said program code is modifiable.

Preferably, the data processing apparatus is a commercially available computer. Further preferentially, the data processing apparatus comprises at least one data processor—i.e. a central processing unit—, in particular a microprocessor, a non-volatile—i.e. in particular permanent—data storage, in particular a hard disk, a read-only memory (ROM) or a drive with a data medium, as well as at least one hardware interface. The data processing apparatus also preferably comprises a volatile electrical data storage, in particular as working memory, preferably a semiconductor memory, in particular with integrated capacitors and/or flip-flops (bistable multivibrators) for data storage, for instance dynamic RAM or static RAM.

In the sense of the invention, a "data storage apparatus" is an apparatus for storing data. Same is in particular designed to form a data link with a further apparatus, particularly a data processing apparatus, and/or comprises a data link to the further apparatus, wherein data can be transmitted to the data storage apparatus from the further apparatus for storage by means of the data link and/or data can be transmitted from the data storage apparatus to the further apparatus for retrieval. Preferably, the data storage apparatus comprises at least one non-volatile memory. Also preferably, the data storage apparatus comprises at least one volatile electrical data storage.

A communication device is preferably configured to transmit and/or receive data, in particular for data exchange over a data connection provided by the communication device, particularly for a remote data link to a remote device. In particular, a unit arranged external of a treatment cart is also referred to as a "remote unit" or external unit, for instance an external user interface. In particular, an apparatus which is not a component part of a control system is also referred to as an external apparatus, for instance an external treatment cart. The data connection, in particular remote data link, can be established by a restricted (in particular intranet) or global network of computers (in particular a WAN and/or the internet). The data connection, in particular remote data link, can also be established by wireless connection, in particular radio link. The data I connection ink, in particular remote data link, can in particular be established by mobile radio connection.

A data connection connects in particular two data processing units, in particular two data processing devices or apparatus, in a way so as to enable the exchange of data between the units, either unidirectionally or bidirectionally. The data connection can be realized in wired or wireless manner, in particular as a radio link. A remote data connection connects in particular two data processing units, particularly two data processing devices, disposed at a distance from one another, thus not being component parts of the same unit, in particular the same treatment cart, user interface device or control system, if the cited units are realized as separate units. A data connection, in particular remote data link, of one unit to another unit is preferably realized by a direct connection between the two units or by an indirect connection of the two units such that a third unit is connected between the two units in order to pass on the data. A remote data connection can in particular be realized by a network of computers with which the units connected by the remote data link are interconnected via the network. The network can be a restricted network, e.g. an intranet, or a global network, in particular a WAN and/or the internet.

In the sense of the invention, an "interface device" serves the connection of two units—in particular including systems, apparatus, devices or mechanisms, particularly having such units—, respectively capable of processing signals, in particular information, particularly data, thus in particular sending and/or receiving. An interface device can comprise at least one hardware interface and in particular be integrated into one physical device unit as a component part.

In the sense of the invention, "hardware interface devices"—or "hardware interfaces" for short—are in particular interfaces between electrical, preferably electronic, units as per the usual understanding in electrotechnology and electronics. In the present case, the term "hardware interface" refers in particular also to the connecting components themselves between at least two electrical units, thus in particular all the component parts which contribute to making the connection possible, e.g. the integrated circuits, electronics and lines via which electrical signals are transmitted between the at least two electrical units. Said two electrical units can in particular be a control system and a release mechanism or two electrical units within one treatment cart. Although not mandatory, a hardware interface can comprise a releasable connecting device, in particular at least one plug, for disengaging and/or restoring the connection. Accordingly and additionally or alternatively, units connected by means of a hardware interface can also work entirely or partially optically and/or the signals between the two units can be optically sent.

In the sense of the invention, "software interfaces" are in particular logical points of contact in a system which are fully or at least partly implemented by software functions, in particular a software system, particularly an information management system. They enable and control, in particular regulate, the exchange of commands and data between different processes and components of the system and/or with another system. Software interfaces can be data-oriented interfaces used only for communication. In this case, a software interface only contains the information—thus in particular the data—to be exchanged between participating system components and/or with a component of the further system.

In the sense of the invention, a "user interface device"—or "user interface" for short—is a device which serves in the communication between a user and a unit—in particular also a system, an apparatus, a device or a mechanism, particularly having such a unit. In particular, the unit can thereby particularly process signals electrically or optically, in particular information, particularly data, thus in particular send and/or receive. The user interface comprises a first communication means, in particular a hardware interface, for communicating with the unit and a second communication means for communicating with the user. Preferably, the first communication means is configured to establish a data connection with the unit and/or comprises a data connection to the unit.

In particular, communication can occur from the unit to the user, thus data transmitted from the unit to the user interface via the first communication means and the user signaled there by means of the second communication means; i.e. in particular the information coded by the data being output. Preferably, such a user interface outputs the information optically, acoustically and/or haptically. Such user interfaces are in particular a display panel, a screen, an indicator light, a loudspeaker, a vibrating alarm or a Braille display.

Additionally or alternatively, communication can in particular also occur in the reverse direction, thus data from the user, in particular one or more user inputs, acquired by means of the second communication means and transmitted to the unit via the first communication means. Preferably, such user interfaces capture the data by means of a sensor technology-based measurement of radiation, in particular electromagnetic radiation such as light or radio waves, sound, in particular ultrasound or sound within the audible range, electrical contacts and/or force or respectively pressure, and/or are designed for user actuation. Such user interfaces are in particular a camera—preferably for gesture control—, an infrared sensor, a microphone—particularly for the audible range, preferably for voice control, or for ultrasonic and together with a corresponding ultrasonic transmitter, preferably for gesture control—, a reader unit—preferably an optical scanner for instance for bar codes or documents, an RFID reader, a magnetic strip reader or a chip reader—, a switch, a control pedal, a keyboard, a computer mouse or a touch-sensitive input surface.

Further preferentially, communication can be made in both directions, wherein the user interface comprises in particular at least one further first communication means and/or at least one further second communication means thereto. In particular, the second communication means can thereby be configured to output data and the further second communication means to capture data; i.e. in particular configured for inputs from the user. Such a user interface is in particular a touch-sensitive screen.

Further advantages, features and possible applications of the present invention are yielded by the following detailed description of at least one example embodiment and/or by the figures. Unless otherwise described or contextually indicated otherwise, the same reference numerals are substantially used to identify equivalent components in the embodiments.

Figure 2:
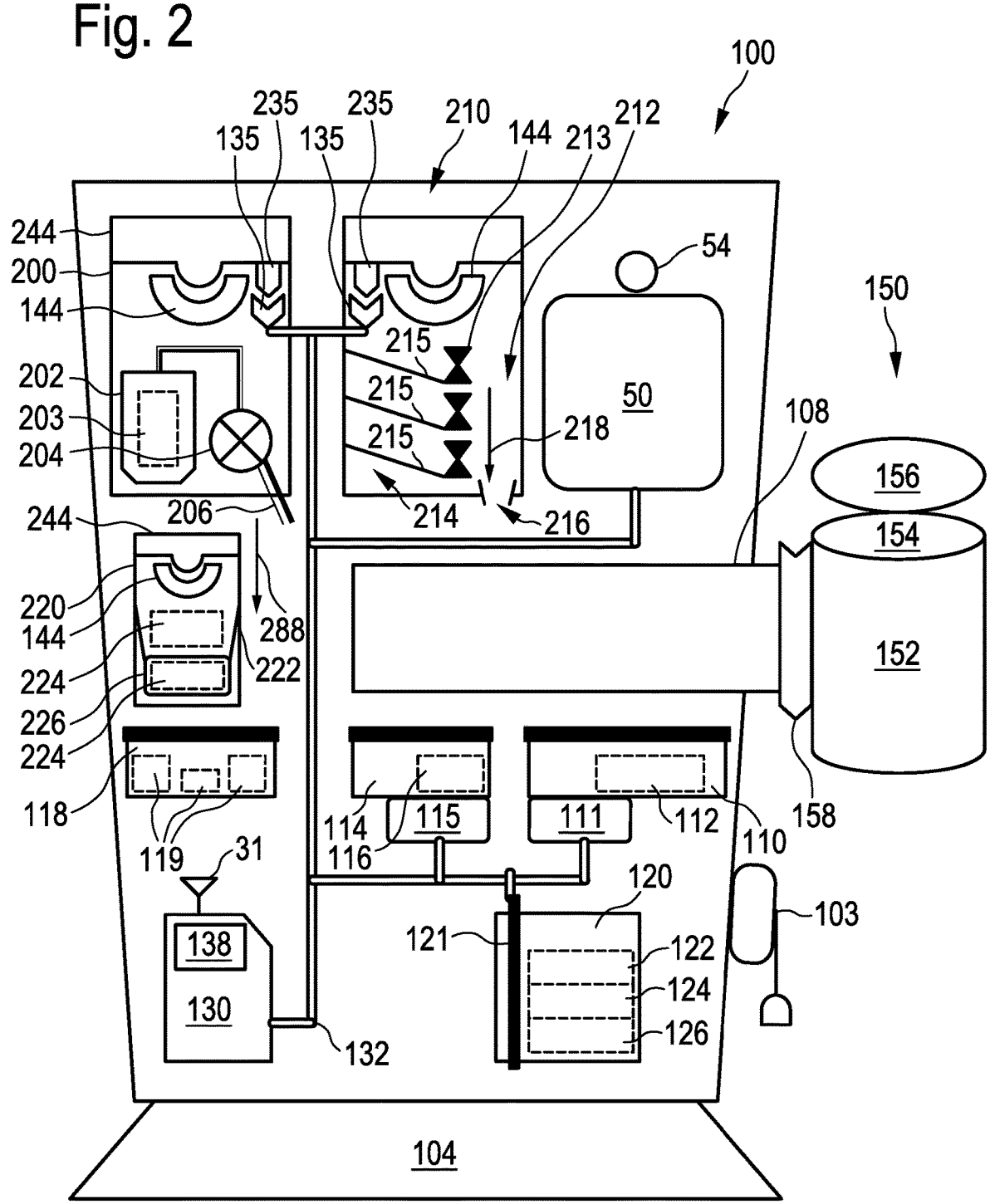
Figure 3:
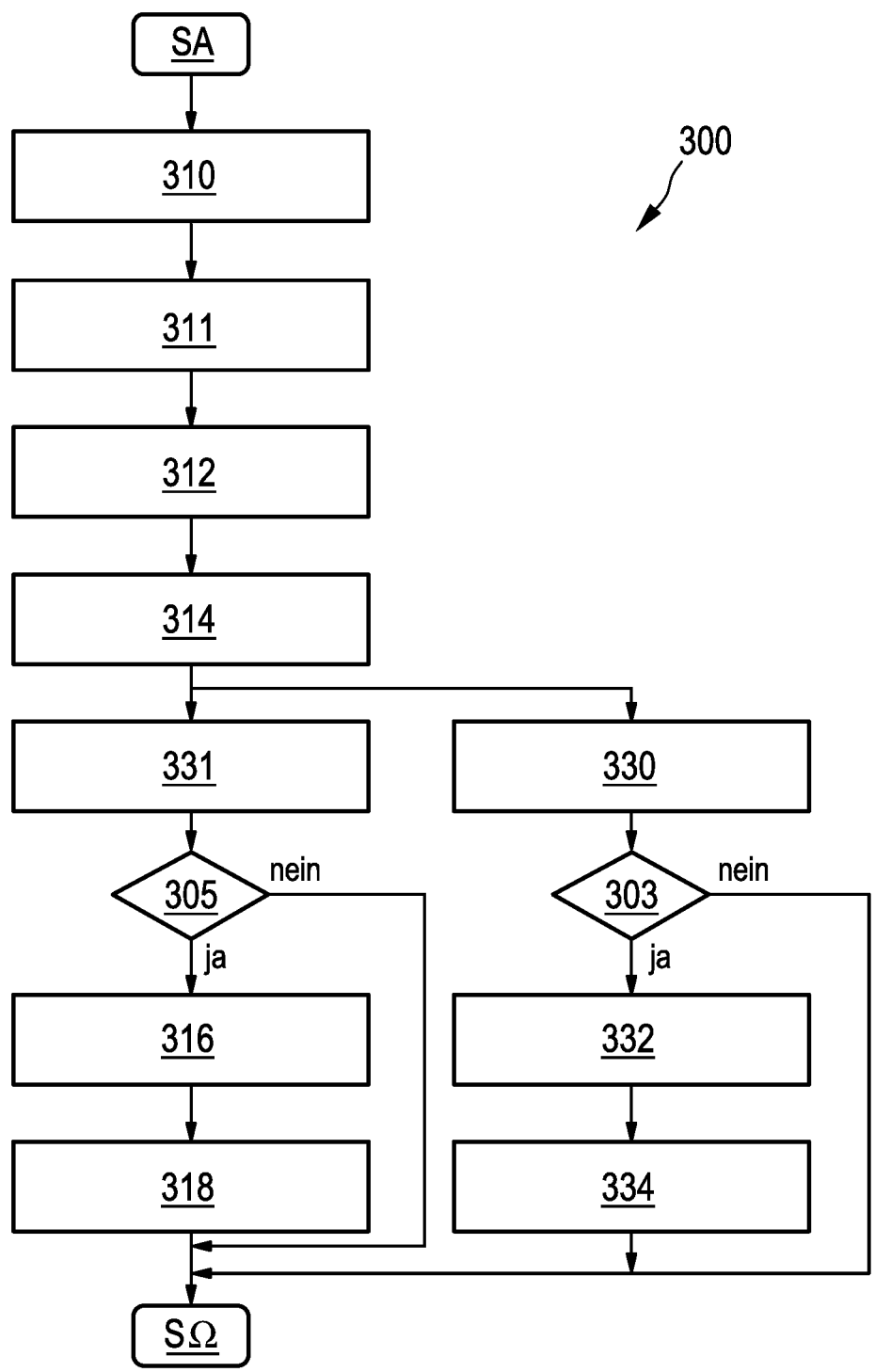

Thereby shown, to some extent schematized:

FIG. 1 an example embodiment of the mobile selection system according to the invention;

FIG. 2 an example embodiment of the treatment cart according to the invention; and FIG. 3 an example embodiment of the inventive method for selecting medical accessories.

FIG. 1 depicts an example embodiment of the inventive mobile selection system 10. The mobile selection system comprises a control system 20, three treatment carts 100, 160, 180 and two user interfaces 50, 52. The mobile selection system 10, in particular the control system 20, comprises one respective data connection 32 each for the treatment carts 100, 160, 180 and the user interface 52 or is at least designed to establish same. The mobile selection system thereby comprises corresponding communication devices 30, 31 for the data connections 32, whereby in particular the communication devices 30 are in each case a component part of the control system 20 or one of the treatment carts 160, 180 or the user interface 52, and/or communication device 31 is a component part of treatment cart 100. The communication devices 30, 31 are preferably designed as network interface devices, in particular for a wireless network—for instance preferably with a so-called Ethernet adapter and/or WiFi adapter—and to establish the data connections 32 over a network, in particular over a local network (LAN/WLAN), a metropolitan area network (MAN) and/or a wide area network (WAN) and/or preferably over the internet and/or further preferably over a virtual private network (VPN)—and thus particularly secure—which is tunneled through another network, particularly the internet.

The control system 20 comprises an accessory database 22 which is designed for data sets on a plurality of medical accessories, a data storage apparatus 24, in particular for said accessory database 22, whereby the accessory database 22 is stored on the data storage apparatus 24, a data processing apparatus 26 and a working memory 28, and is designed to operate the accessory database 22. Preferably, the accessory database 22 is configured as a relational database, in particular an SQL database able to be queried by an SQL query. Preferably, the data storage apparatus 24 for the accessory database 22 is designed as a non-volatile data storage, in particular as a magnetic hard drive (HDD) or a solid state disk (SSD) or as an array (RAID) thereof. Preferably, the data processing apparatus 26 is designed as a microprocessor or at least comprises one. Preferably, the working memory 28 is designed as a volatile data storage, in particular a volatile electrical memory, in particular dynamic RAM (DRAM), particularly double data rate synchronous dynamic random-access memory (DDR-SDRAM). In particular, the data processing apparatus 26 with the microprocessor, the working memory 28 and the data storage apparatus 24 can be configured as a commercially available computer on which the accessory database 22 is stored and be further designed to operate the accessory database; thus the database and the program code of the accessory database 22 are in particular stored on the computer, particularly the data storage apparatus 24, and the computer is designed to load the program code into the working memory and run it as well as access the database by executing the program code in a predetermined manner, in particular upon database queries.

The treatment carts are arranged at three geographically different treatment sites 80, 86, 88, wherein it is clear that the treatment carts can also be transported, in particular moved, to other treatment sites. In particular, treatment sites 86 and 88 can be within a clinical center and/or treatment site 80 can be the residence of a patient. One advantage of the treatment cart 100 being disposed at the residence 80 of the patient can in particular be that of the patient being supplied with medical accessories for a treatment to be performed at home. This can be particularly advantageous in the treatment of chronic illnesses, wherein frequent and/or regular stays in a clinical center can be avoided or at least reduced. Thus, in particular achieved is a dialysis treatment of a dialysis patient being able to be performed as home dialysis and/or the patient supported in the home dialysis by means of the storage as well as releasing of the medical accessories required thereto. One advantage of treatment cart 160 being disposed at treatment site 86, or respectively treatment cart 180 at treatment site 88, can in particular lie in medical accessories being able to be released at the respective treatment sites, for instance in different areas or rooms in one or more wards of a clinic, and the treatment carts 160, 180 being able to be moved to different treatment sites when needed. Furthermore, the control system 20 or components thereof, in particular the accessory database 22, the data storage apparatus 24, the data processing apparatus 26 and/or the working memory 28, can be disposed at another geographically different location than the treatment sites 80, 86, 88.

The user interface 50 is non-detachably, preferably integrally, connected to the treatment cart 100. The user interface 52 is, as illustrated in FIG. 1 as an example, arranged at the treatment site 88 and not physically connected to any treatment cart. Preferably, the user interface 52 is configured as a treatment cart module and can be detachably connected to one of the treatment carts by means of a connecting apparatus for same, in particular by means of a connecting apparatus 184 of the treatment cart 180.

To operate the treatment carts 100, 160, 180, the user interfaces 50, 52 are respectively allocated or allocatable to a treatment cart. To that end, the control system 20 preferably comprises an allocation rule for user interfaces and a data storage apparatus for same, wherein the data storage apparatus is in particular data storage apparatus 24 and/or working memory 28. The allocation rule is configured to allocate a user interface 50, 52 characterized by a user interface identifier to a treatment cart 100,160, 180 characterized by a treatment cart identifier on the basis of allocation data stored on said data storage apparatus. Preferably, the respective allocation can be made via a user input. The user can thus be shown a list of treatment carts 100, 160, 180 available in the system, whereupon he can select a treatment cart in the list, for instance by tapping on a user interface configured as a touch-sensitive screen and, as a result of this selection, the control system 20 applicably adapts the allocation data and the user interface 52 is assigned to the selected treatment cart. Additionally or alternatively, a user interface is or can be assigned to a treatment cart by being connected to the treatment cart, in particular physically. Thus, the user interface 50 is preferably allocated to the treatment cart 100 by virtue of its non-detachable connection, wherein this allocation cannot be modified in the allocation rule or respectively exists independently of the allocation rule or, alternatively, the allocation can also be overwritten by an appropriate user input.

The user interfaces 50, 52 are designed for one or more inputs from a user, by means of which a treatment to be performed is specified and on the basis of same, the control system 20 determines a treatment identifier associated with the treatment to be performed as a result of the inputs. The user interfaces 50, 52 preferably have a touch-sensitive screen for the inputs and outputs. Preferably, the user interface 50 is configured as one such touch-sensitive screen and is internally connected in the treatment cart 100 to further components of the treatment cart 100 and/or the control system 20. For the sake of clarity, such internal connections are not depicted in FIG. 1. Preferably, the user interface 52 is designed as a mobile terminal, in particular as a smartphone or tablet PC and comprises one of the communication devices 30. Alternatively or additionally, the user interfaces 50, 52 can also comprise or consist of further input/output units such as control dials, push-buttons, a keyboard, a computer mouse and/or a microphone and/or loudspeaker, electrical indicator lamps and/or an LCD display.

The user interfaces 50, 52 are designed to transmit the inputs, in particular the inputs for determining the treatment identifier of the treatment to be performed, to the control system 20 over one of the data connections 32. Preferably, the user interface 50 is internally data-linked to further components of the treatment cart 100 to this end and in particular indirectly or directly to the communication device 31, particularly by signal lines. User interface 52 preferably comprises one of the communication devices 30 to that end and is thus independent of the treatment carts. This advantageously enables user interface 52, while also being designed for inputs or while inputs are being made respectively, to be positioned at a different geographic location as the associated treatment cart, respectively independently of the treatment cart's location. In particular, the user interface 52 can thus be allocated to the treatment cart 160 located at treatment site 86 and inputs can also be made for same at user interface 52 while user interface 52 is located at treatment site 88.

Preferably, at least one of the user interfaces 50, 52, in particular user interface 52, is designed to acquire one or more inputs from a user by means of which a patient to be treated is specified and, on the basis of same, the control system determines a patient identifier associated with the patient to be treated as a result of said inputs. To that end, the user interface 50, 52 can in particular be designed to display one or more input fields for characteristics identifying the patient to be treated on the touch-sensitive screen—for instance name or patient number—and capture inputs relative to the input fields and transmit them to the control system 20. The user interface 50, 52 can also in particular comprise a reader unit to that end, preferably for instance an insurance card reader, a bar code scanner or a document scanner, with which characteristics which identify the patients to be treated can be read in.

The treatment cart 180 comprises a storage device 190 having three storage areas 192, 194, 196, each for a respective accessory type of the plurality of medical accessories. In particular, the treatment cart 180 is schematically depicted in FIG. 1 as a side section through the treatment cart. Particularly when the treatment cart 180 is equipped for a dialysis treatment, in particular for the cannulation to thereby be performed—for instance of an AV fistula—storage area 192 can thereby comprise one or more cannulas, storage area 194 one or more Seldinger wires, and storage area 196 one or more catheters. In addition, the treatment cart 180 has a release mechanism 191 for releasing medical accessories, in particular for the storage device 190. The treatment cart 180 further has at least two, preferably four, wheels 182. Preferably, the treatment cart 180 additionally comprises one of the communication devices 30 or is at least physically connected to same. In addition, the treatment cart 180 can, as described above, comprise a connecting apparatus 184 for a user interface. Preferably, the connecting apparatus 184 is configured to at least partly accommodate a user interface, particularly user interface 52, and connect the treatment cart 180 to the user interface in form-fit and detachable manner. Preferably, the storage device 190 is designed, as is illustrated in FIG. 1, as a drawer or at least comprises same. Also preferably, the release mechanism 191 for the storage device 190 is configured as a motorized cable pull or as a motor-driven spindle and designed to extend the drawer 190 out and/or retract it again pursuant to the control of the control system 20.

For treatment cart 180, the control system 20 is designed to implement a selection method having the following method steps. In one method step, the treatment identifier of the treatment to be performed is determined on the basis of the inputs at the user interface 52, provided same is allocated to the treatment cart 160. In a further method step, an accessory set parameter is determined on the basis of the accessory database 22 and on the basis of the treatment identifier of the treatment to be performed, whereby the accessory set parameter characterizes a medical accessory set from among one or more of the medical accessories suitable for the treatment to be performed. In particular, the accessory set parameter identifies the positions of the storage areas 192, 194, 196 which are equipped with the respectively suitable medical accessories—i.e. in particular are for the respective accessory types—and preferably the distance for the drawer to which the drawer needs to be pulled out in order for the respective storage area to be made accessible; i.e. in particular release the respective medical accessories stored there. The control system 20 is additionally designed to control the release mechanism 191 based on the accessory set parameter such that the release mechanism 191 releases those medical accessories characterized by the accessory set parameter. Preferably, the control system 20 controls the release mechanism 191 for the drawer 190 such that it in each case extends out the drawer by the distance as characterized by the accessory set parameter and thus makes the respective storage area for the respective medical accessories of the accessory set accessible.

For the supplying of electrical energy, the treatment cart 180 preferably comprises an electrical energy storage 183, in particular one or more rechargeable batteries. Preferentially and additionally or alternatively, the treatment cart 180 can also comprise a connecting device to the power supply system, in particular a plug with a cable or cable reel.

Correspondingly, treatment cart 160 comprises a storage device 170 having three storage areas 172, 174, 176, a release mechanism 171, wheels 162 and preferably one of the communication devices 30. In particular, the treatment cart 160 is schematically depicted in FIG. 1 as a side section through the treatment cart. Particularly when the treatment cart 160 is equipped for a dialysis treatment, in particular for the preparation of and performing of a cannulation, the storage areas can thereby respectively comprise medical accessories of the following accessory types: storage area 172, disinfecting wipes; storage area 174, bandages/adhesive strips with an analgesic agent; and storage area 176, accessory sets for the cannulation, each with a cannula, a Seldinger wire and a catheter.

For the supplying of electrical energy, the treatment cart 160 preferably comprises an electrical energy storage 163, in particular one or more rechargeable batteries. Preferentially and additionally or alternatively, the treatment cart 160 can also comprise a connecting device to the power supply system, in particular a plug with a cable or cable reel.

Treatment cart 160 moreover exhibits a repository device 168 having a disinfectable work surface and a detection system 166. The work surface of the repository device 168 can be disinfected prior to the treatment and/or prior to sub-treatments of the treatment and/or individual treatment steps of the treatment. To that end, the treatment cart 160 can in particular comprise a disinfecting apparatus, not shown in FIG. 1. The work surface is provided for the respectively required medical accessories to be placed onto prior to the treatment or prior to individual treatment steps and thus be immediately available and/or within reach for the treatment or the respective treatment step. The detection system 166 detects an individual 66 involved in the treatment and/or medical accessories which the individual 66 will use and/or which lie on the work surface by means of one or preferably multiple image sensors, preferably three-dimensionally.

In one preferential variant, the detection system 166 is designed to utilize the image sensors as sensor devices for identification data and use same to capture identification data enabling a biometric identification of the individual 66. In addition, the control system 20 is preferably designed to implement an identification method and identify the individual 66 on the basis of the detected identification data or, otherwise, determine the individual 66 as being a non-identified person. The control system 20 is further designed to register the individual 66 in the system and determine a user identifier as a function of successfully identifying the individual 66, whereby registered users are preferably assigned specific authorizations or particularly a non-identified individual or respectively unregistered user has no authorization, is thus an non-authorized user.

In one preferential variant, the detection system 166 is designed to determine the respectively performed treatment step on the basis of the detected use of the medical accessory and/or the medical accessories lying on the work surface or taken from same respectively as well as preferably on the basis of the treatment to be performed, provided same was specified.

In accordance with the preceding description in respect of the control system 20 for treatment cart 180, the control system 20 for treatment cart 160 is designed to implement a corresponding selection method and control the release mechanism 161. In the process, preferably a plurality of accessory set parameters are determined in the selection method, whereby one of same corresponds to the preceding description and at least one further of same characterizes the storage device 170 such that multiple storage devices can be addressed.

The control system 20 is thereby preferably furthermore designed to implement the selection method only given registered users and pursuant to their authorization and only release those medical accessories for which the respective user is authorized. In particular, the selection method to that end further comprises the method step of verifying whether the registered user is authorized for the medical accessories characterized by the accessory set parameter. Preferably, data sets are stored in the accessory database for this type of verification which correlate a medical accessory with one or more users or user groups authorized for said medical accessory or specific authorizations authorized for said medical accessory. In particular, an accessory set parameter is determined in the selection method which characterizes whether the user is authorized for the accessory set and/or for which of the medical accessories of the accessory set.

The control system 20 is also preferably designed to implement an assist method, in particular as part of the selection method. In one method step of the assist method, the detection system 166 determines an assistance parameter characterizing the treatment step to be performed of the treatment to be performed and determines an assistance parameter which characterizes the medical accessories required for the respective treatment step, or alternatively or additionally, determines, particularly in the selection method, one or more accessory set parameters allocating the medical accessories of the accessory set to a respective treatment step.

Lastly, the control system 20 is designed to control the release mechanism 171 so as to release those medical accessories characterized by the accessory set parameter and preferably release that respective part of the medical accessories of the accessory set as required pursuant to the assistance parameter and accessory set parameter for the respective treatment step to be performed and/or for which the user is authorized.

In one variant, the control system 20 is designed to control the release mechanism 171 so as to release the medical accessories for a series of treatment steps—and not just for the respective treatment step to be performed. This thereby advantageously enables the medical accessories to be placed onto the disinfectable work surface of the repository device 168 in advance so that the storage area does not need to be accessed during the performing of the series of treatment steps.

In particular, the assist method can further comprise a method step of determining an assistance parameter which characterizes whether the disinfectable work surface of the repository device 168 has been disinfected—preferably for instance prior to beginning the treatment, prior to, after or during specific treatment steps, or at the end of the treatment—and the control system 20 is designed to control the disinfecting apparatus for the repository device 168 on the basis of the assist parameter such that it disinfects the work surface of the repository device 168 if same is to be disinfected as per the assist parameter.

Thus, in particular, when a dialysis treatment of a patient with an AV fistula has been established as the treatment to be performed, the individual 66 can first be recognized.

Should this individual 66 be the patient to be treated, the control system 20 controls the release mechanism 171 so as to output the medical accessories from storage areas 172 and 174, in particular thus drive out the drawer far enough that these two storage areas 172 and 174 are accessible to the user 66, thus the patient. The patient can thereupon extract a disinfecting wipe out of the storage area 172 and disinfect the area of his skin with the AV fistula. The patient can thereafter extract a bandage having an analgesic agent out of the storage area 174 and stick it on the skin area. The user 66, thus the patient, is not initially authorized for any further treatment steps. A physician, who then intervenes, can at this point be recognized as the individual 66 involved in the treatment and be authorized for further treatment steps. The control system 20 thereupon preferably controls the disinfecting apparatus so as to disinfect the work surface of the repository device 168. The control system 20 thereafter controls the release mechanism 171 to release further medical accessories from the storage area 176, in particular one of the accessory sets for the cannulation; the release mechanism 171 is in particular thus controlled by the control system 20 so as to extend out the drawer far enough for storage area 176 to be accessible. The physician 66 can then extract the accessory set with the cannula, the Seldinger wire and the catheter from the storage area 176 and place it on the work surface of the repository device 168, whereby these medical accessories are then available to him for the further treatment steps, in particular for the cannulation.

The treatment cart 100 comprises a plurality of storage devices 110, 114, 118, 120, at least one release mechanism—not shown in FIG. 1—, a repository device 108, a connecting apparatus 104 for a transport apparatus 102 which is separable from the treatment cart 100, a drive apparatus 130, two connecting apparatus 144 for treatment cart modules, a disposal apparatus 150 and preferably the communication device 31 and/or preferably the user interface 50. The treatment cart 100 is in particular schematically depicted in FIG. 1 as a partly perspective view from the front/top of a frontal partial section through the treatment cart. Thus, in particular the control device 130 is preferably arranged in a housing of the treatment cart 100 and therefore not normally visible in a frontal view.

In particular, the treatment cart 100 as well as the control system 20 and/or the selection method correspond at least in part, in particular substantially, to the description in respect of treatment carts 160 and 180. Treatment cart 100 itself, however, thereby exhibits no wheels for transport but rather the connecting apparatus 104 for the transport apparatus 102. For transport, the treatment cart 100 can be detachably connected to the transport apparatus 102 which is in particular not a component part or at least not a permanent component part of the treatment cart 100. This connection is preferably of form-fit and/or force-fit configuration, in particular as a latching mechanism. To that end, the connecting apparatus 104 preferably exhibits a recess, particularly at least three recesses, and the transport apparatus 102 comprises the thereby corresponding hooks, each preferably being provided with a spring mechanism so that the hooks will snap into the recesses when disposed therein. Alternatively or additionally, the transport apparatus 102 and the connecting apparatus 104 can also be detachably connected by means of one or more screw connections.

Furthermore, the at least one release mechanism is at least partly controlled by the drive apparatus 130. To that end, the control system 20 is preferably data-linked to the drive apparatus 130 via the communication device 31 and the drive apparatus 130 actuates the at least one release mechanism at least partially on the basis of the data it receives from the control system 20 over the data connection 32 by means of the communication device 31.

FIG. 2 shows a treatment cart 100 in particular for set-up at the residence of a patient, in particular for home dialysis, as an example embodiment of the treatment cart according to the invention. This in particular corresponds to treatment cart 100 from FIG. 1. The treatment cart 100 can be connected to a transport apparatus—not shown in FIG. 2—by means of a connecting apparatus 104 of the treatment cart 100 and thus transported to the site where it is to be set up, in particular the patient's residence. The treatment cart 100 is in particular schematically depicted in FIG. 2 as a partly perspective view of a frontal partial section through the treatment cart. FIG. 2 hereby uses dashed lines to schematically indicate in particular the storage areas and/or medical accessories located within a storage device or a treatment cart module. The treatment cart 100 also preferably comprises a connecting device 103 to the power supply system, in particular a plug, a power cable and a cable reel for the power cable for the supplying of the treatment cart 100 with electrical energy. In addition, a transport apparatus for the treatment cart can comprise an electric energy storage so that the treatment cart can also be supplied with electrical energy while being transported by the transport apparatus—thus in particular a plug of the connecting device 103 not remaining in a power outlet.

The treatment cart 100 moreover comprises two storage devices 110 and 114, preferably each configured as a drawer, having in each case exactly one storage area 112/116 as well as one release mechanism 111 for storage device 110 and one release mechanism 115 for storage device 114. Preferably, release mechanism 111 comprises or consists of a motorized cable pull, a motor-driven spindle or a rack-and-pinion drive, whereby same advantageously enables the fully automated opening and closing of the storage device 110, in particular the drawer, for the releasing of medical accessories stored in storage area 112 and particularly the subsequent closing of the drawer again thereafter. Preferably, the release mechanism 115 comprises or consist of an electrically controllable magnet lock and, particularly for the drawer, one or more—particularly passive—guide rails, whereby same advantageously enables the electrical release of the storage device 114 so that it can be, in particular manually, opened and medical accessories which are stored in the storage area 116 can thus be released in controlled manner. Preferably, storage area 116 is thereby provided for emergency medication which the patient may only access after physician authorization.

According to one preferential semi-automated variant, the treatment cart 100 additionally comprises a storage device 118, preferably configured as a drawer, having one or more storage areas 119. This storage device 118 is designed for manual operation and the treatment cart 100 has no release mechanism for same. Instead, medical accessories in the storage areas 119 of the storage device 118 can be withdrawn and/or stored there independently of release mechanisms, a selection method, a control and/or a mobile selection system. The storage areas 119 are particularly suitable for frequently used and/or non-safety-relevant medical accessories and/or for medical accessories used for a plurality of treatments.

Moreover, the treatment cart 100 preferably comprises a storage device 120, configured as a compartment with doors, having three storage areas 122, 124 and 126 as well as a release mechanism 121 for same, as illustrated as an example in FIG. 2. Preferably, the release mechanism 121 comprises an indicator lamp—for instance an LED—whereby the indicator lamp signals when a medical accessory, for which the storage device 120 has a storage area 122, 124 or 126 for its type, is characterized by the accessory set parameter. In the variant as compartment with doors, the release mechanism 121 additionally comprises a handle so that the compartment's doors can be opened by means of the handle, in particular upon being signaled by the indicator light. This allows supporting a user, in particular the patient, during the selection and/or extracting of the medical accessories required for the treatment to be performed, in particular without limiting his access to the medical accessories stored in the storage device 120. Additionally, a storage device configured as a compartment enables a plurality of medical accessories, also of different sizes—for instance even medicine devices—to be stored.

The treatment cart 100 furthermore exhibits a user interface 50—in particular a touch-sensitive screen—, a camera module 54, a repository device 108 with disinfectable work surface, and one or more connecting apparatus 144 for treatment cart modules, whereby at least the user interface 50 and preferably further components, in particular one of the connecting apparatus 144, is physically connected, in particular integrally, to the treatment cart 100.

The treatment cart 100 comprises a drive apparatus 130 having a communication device 31 and is designed to establish a data connection to a control system of a mobile selection system via same or comprises such a data connection. Here, the control system at least partly controls the release mechanisms via the drive apparatus 130. Preferably, the drive device 130 receives the accessory set parameters which the control system determined in a selection method, and applies them to a concrete control, in particular for the respective storage devices and/or treatment cart module with medical accessories. In particular, the drive apparatus 130 can comprise one or more control loops to that end, which is advantageous, particularly compared in particular to direct control via the control system, particularly in respect of time requirements and/or feedback times. In particular, the drive apparatus 130 can be a commercially available computer equipped for the control. Preferably, the drive apparatus 130 electrically drives the release mechanisms and further components of the treatment cart 100 as applicable and to that end comprises a data bus 132, preferably configured as a universal serial bus (USB). To connect to treatment cart modules, the data bus comprises in particular one or more connecting devices, in particular connecting units 135, particularly plugs or sockets. At least one of the connecting units 135 is thereby adjacently arranged to one of the connecting apparatus 144 for treatment cart modules. The data bus 132 can also data-link further components of the treatment cart 100—for instance the user interface 50 or the camera module 54—, preferably electrically, whereby these connections are only depicted in part in FIG. 2 for better clarity. It is further preferential for the data bus to be designed to supply energy, particularly electric current, to components of the treatment cart 100, in particular one or more of the release mechanisms and/or one or more treatment cart modules and/or the user interface 50 and/or the camera module 54.

Additionally, the treatment cart 100 comprises a disposal apparatus 150. The disposal apparatus 150 has a disposal bin 152, an opening 154 for objects to be disposed of, in particular medical accessories, a locking mechanism 156 for the opening, and a weight-based or change-in-weight-based sensor system 158.

Preferably, the drive apparatus 130 together with the sensor system 158 is thereby configured as a treatment detection system. Preferably, the drive apparatus 130 further comprises a chronometer thereto, in particular a clock or an apparatus for synchronizing to a global time—for instance GPS or DCF77—and is designed to determine for a defined treatment, and preferably additionally for defined treatment steps as are to be respectively performed, a change in weight as well as the interval of time between the weight change and a previous weight change or an initialization and, based thereon, determine: which treatment step has been performed and/or whether the treatment step was successfully performed. To that end, the control system—or the drive apparatus 130 as a component part of the control system—preferably implements an assist process, whereby one or more treatment parameters are determined in a procedural step which characterize the treatment to be performed, its treatment steps and/or usual periods of time needed to perform the treatment steps and/or usual weights of the medical accessories required for the respective treatment steps, particularly in used and unused state. The control system provides these treatment parameters to the drive apparatus 130, transmitting them to that end to the drive apparatus 130 via the communication device 31, preferably by means of the data connection.

In one preferential variant, the control system or the drive apparatus 130, in particular as a component of the control system, comprises a data storage apparatus 138 for assistance information. Preferably, this assistance information is in each case image sequences or videos regarding the treatment steps to be performed. The following procedural steps are implemented in the assist process: Determining a first treatment step to be performed based on the treatment to be performed pursuant to a selection method and/or by means of the treatment detection system in a first procedural step; Retrieving assistance information regarding the respective treatment step to be performed from the data storage apparatus 138 and outputting said assistance information by means of the user interface 50 in the second procedural step; Determining by means of the treatment detection system whether the treatment step has been performed and whether it was successful in a further procedural step; If so, continuing with the second procedural step for the next treatment step of the treatment to be performed and, otherwise, continuing with the second procedural step for the unsuccessfully performed treatment step. The process is thereby ended when an abort criterion is present, in particular after the successful performing of all treatment steps. The drive apparatus 130 and/or the control system can also be designed to release those medical accessories needed for the respective treatment step to be performed, and in particular repeatedly release medical accessories when a treatment step has not been successfully performed. Additionally or alternatively, the control system or the drive apparatus 130 is preferably designed to receive an input from the user, in particular the patient, which characterizes an unsuccessfully completed treatment step and thereupon continue the assist procedure with the second procedural step for the unsuccessfully completed treatment step. The same applies to an input regarding a successfully completed treatment step. This thereby advantageously enables the automatic detection to be supplemented by a manual input, whereby on the one hand, the assistance is automatic and the user convenience can be increased and, on the other hand, if an error occurs during the automatic detection, it can be manually corrected.

In a dialysis treatment with an AV fistula or AV graft, that which is in particular stored and/or output as assistance information can be: an illustration of the medical accessories and their use in disinfecting the area of skin to be cannulated; an illustration of cannula insertion; an illustration of catheter introduction; and/or an illustration of fixing the catheter, particularly with an adhesive tape or bandage. With respect to the insertion, the control system is preferably designed to determine the respective puncture site and in particular the insertion angle—thus for instance pursuant to the rope ladder technique or the buttonhole technique—on a patient-specific basis. In the rope ladder technique, a new puncture site along the blood vessel; i.e. in particular the AV fistula/AV graft, located at a distance from the previous puncture site, e.g. typically about 2 cm, is determined for each insertion. In the buttonhole technique, the same puncture site is used repeatedly, thereby particularly always at the same insertion angle, such that in particular a pinhole similar to the hole for an earring is formed. Only after a predetermined number of insertions/cannulations is a new puncture site ultimately selected.

The drive apparatus 130 is preferably furthermore designed to detect the performing of a treatment and/or the user, in particular the patient, by means of the camera module 54. Preferably, the drive apparatus 130 is designed to store the thus acquired data on a data storage apparatus of the treatment cart 100 and/or transmit it to a control system of a mobile selection system via a data connection, in particular by means of communication device 31. This advantageously enables the treatment to be reconstructed at a later point in time, for instance for increasing the quality, and/or observing of the patient during treatment and being able to, if needed, provide remote assistance to him in performing the treatment or specific treatment steps.

Lastly, the treatment cart 100 is preferably equipped with treatment cart module 200 and/or treatment cart module 210 and/or treatment cart module 220. The and/or treatment cart modules 200, 210, 220 each have a connection point device 244 with at least one connecting point for the form-fit and/or force-fit connection to the respective connecting apparatus 144 of the treatment cart 100. Preferably, a treatment cart module, in particular treatment cart module 200 and treatment cart module 210, comprise a connecting unit 235 for a data bus. The connecting unit 235 is thereby in particular designed to connect to a connecting unit 135 of the data bus 132, in particular as a socket/plug. The connecting unit 235 is thereby in particular also at least arranged adjacently to the connection point device 244 such that when the connection point device 144 is arranged adjacent to the corresponding connecting apparatus 144 of the treatment cart, the connecting unit 235 is also arranged adjacently to corresponding connecting unit 135 and thus connectable. Preferably, the connection point device 244 and the connecting unit 235 are arranged and configured such that when the connection point device 244 is connected to the corresponding connecting apparatus 144, connecting unit 235 is also connected to connecting unit 135.

Other components of the treatment cart 100, in particular one of the storage devices 110, 114, 118, 120 or the disposal apparatus 150, can also be configured as a treatment cart module. For a storage device designed as such a treatment cart module, particularly a drawer together with a corresponding release mechanism, the treatment cart can preferably comprise a connecting chute designed to receive the treatment cart module of in particular at least the drawer and the release mechanism.

The treatment cart module 220 comprises a manual dispenser apparatus, in particular a glove box, or consists of a manual dispenser apparatus configured as a treatment cart module. Same comprises a chute 222 for storing medical accessories 224, in particular disposable gloves packaged in pairs, and an opening 226 for extracting the medical accessories. The chute 222 is thereby oriented with respect to its longitudinal axis 228 and the opening 226 arranged and/or both disposed, at least when the treatment cart module 220 is connected to the treatment cart 100 for the customary use, such that as soon as the medical accessory 224 arranged in the chute 222 near the opening 226 is removed through the opening 226, a further medical accessory 224 falls or slides through the chute 222 to the opening 226 along the longitudinal axis 228. Since the manual dispenser apparatus is operated manually, thus in particular has no release mechanism, the treatment cart module 220 preferably has no connecting unit 235 for the data bus. Alternatively and preferentially, the treatment cart module 220 can comprise a connecting unit 235, in particular in order to detect the filling level of the manual dispenser apparatus by means of sensors and transmit this to the drive apparatus 130 over the data bus 132.

The treatment cart module 200 comprises a dosing apparatus or consists of a dosing apparatus configured as a treatment cart module. As an example embodiment, the dosing apparatus is designed to dose a liquid disinfectant—for instance preferably a liquid with water, ethanol, 2-phenoxyethanol, propan-1-ol, propan-2-ol, didecyldimethylammonium chloride and/or mecetroniumetil sulfate. It has a storage device 202 designed as a container for the disinfectant, a separating apparatus 204, designed as a pump with an intake, and an outlet 206. In particular, therefore, the interior of the container 202 is the storage area 203 for the disinfectant. The pump 204 is fluidly connected to the container 202 by way of the intake such that it can pump out doses of the disinfectant stored in the container. In addition, the pump is fluidly connected to the outlet 206 so as to be able to release, in particular spray out, a pumped disinfectant; i.e. in particular one dosage of the disinfectant, via the outlet 206.

Preferably, the outlet 206 is oriented so that the disinfectant sprays toward the repository device 108. This advantageously enables the disinfecting of the work surface of the repository device 108 and/or allows the disinfecting of further objects or body parts, in particular hands, when they are held in the area between the outlet 206 and the repository device 108.

Furthermore, the selection method, for the implementation of which the control system is designed, further comprises the following method steps. One method step of the selection method verifies whether the accessory set parameters characterize a medical accessory of a dosable accessory type; i.e. here in particular the disinfectant. Should this be the case, a dosing parameter is determined in a further method step which characterizes the dosable medical accessory; i.e. here in particular the disinfectant, and/or a dosing parameter is determined which characterizes the required dose for the accessory set. The dosage can in particular be the liquid-related or weight-related volume of a disinfectant. Furthermore, the control system is designed to control the pump 204 on the basis of the dosing parameter and preferably the accessory set parameter such that the pump 204 pumps out a portion of the disinfectant as required by the dosage from the container 202. Preferably, the control ensues via a data connection and by means of the drive apparatus 130 which in turn activates the pump 204 via the data bus 132 and via the connecting unit 135 and the corresponding connecting unit 235 connected thereto. The actuating can thereby be a signal to operate and subsequently stop the pump or, alternatively, a signal which codes the dosage; i.e. the amount to be dispensed, whereby the signal is processed by a data processing device of the dosing apparatus, or the treatment cart module 200 respectively, and transformed into a control signal for the pump—i.e. in particular: Operate pump, Wait a predetermined time interval and cease pump operation.

The treatment cart module 210 comprises a storage device 214, in particular as a storage device of the treatment cart 100, having one or more, in particular three storage areas 215 as illustrated in FIG. 2 as well as a release mechanism, in particular as a release mechanism of the treatment cart, which is designed as a separating apparatus. The storage areas 215 are each in particular provided for exactly one medical accessory, wherein the storage device 214 preferably comprises storage areas for one or more accessory types. The separating apparatus comprises a chute 212, an opening 216 for the release of a selected medical accessory, and a respective segregating element 213 for each of the storage areas 215. Preferably, the segregating elements 213 are designed as flap mechanisms having an adjustable flap so that upon actuation to separate out the medical accessory stored in the respectively corresponding storage area 215, the flap opens, the respective storage area 215 is opened to the chute 212, the medical accessory stored in the respective storage area 215 slides or falls toward the chute 212 and along the longitudinal axis 218 of the chute 212 to the opening 216. Furthermore, the medical accessory can pass through opening 216 and thus be dispensed at a supplying area, in particular below the opening 216. In addition, the treatment cart module 210 is preferably arranged at the treatment cart 100 such that a medical accessory which is dispensed through the opening 216 ends up on the work surface of the repository device 108.

The control system is furthermore designed to control the separating apparatus of the treatment cart module 210 so as to, provided the accessory set parameters characterize a medical accessory for which the storage device 214 has a storage area 215, extract said medical accessory out of the storage area 215, in particular by actuating the segregating element 213 corresponding to the storage area 215, and dispense it via the chute 212 as well as opening 216 to the supplying area, in particular the work surface of the repository device 108. Preferably, the control ensues by means of drive apparatus 130 and as per the preceding description relative to the treatment cart module 100.

FIG. 3 depicts an example embodiment of the inventive method 300 for selecting medical accessories. Method steps of this method 300 can also be method steps of the selection method and/or the assist process according to the example embodiments pursuant to FIG. 1 or FIG. 2. One embodiment of the inventive mobile selection system can also be configured to implement such a method 300. One or more treatment carts—for instance treatment carts 100, 160, 180 as per FIGS. 1 and/or 2—are provided for the method 300 or as part of the method 300, each comprising one or more storage devices and at least two respective storage areas of the storage devices, each for a plurality of medical accessories. In particular, at least one, preferably each of the storage areas are thereby provided for, and in particular configured for, one or more medical accessories of respectively exactly one accessory type of the plurality of medical accessories.

The method 300 comprises method steps 310, 312, 314, 316, 318, 330, 331, 332, 334 and preferably method step 311. The method 300 begins at process start SA and ends at process end SΩ, whereby one or more method steps, in particular a sequence of method steps, and preferably the entire method can be repeated.

In a first method step 310, one or more inputs of a user is detected, by means of which the at least one treatment to be performed and preferably the patient to be treated is specified. The detection ensues via a user interface which is data-linked to a control system, in particular a mobile selection system. The method 300 can thereby preferably stay in a wait loop or event-controlled loop until the inputs have been made and/or until an abort criterion which characterizes a repeating of method step 310 or the process end SΩ is fulfilled—preferably for instance by means of a user input to run method step 310 again or to end the method 300, and/or after a predetermined period of time has passed.

Preferably, a patient identifier of the patient to be treated is determined in a further method step 311 on the basis of said inputs and by means of the control system, provided the inputs specify the patient to be treated.

In a further method step 312, a treatment identifier of the treatment to be performed is determined on the basis of the inputs by means of the control system. In particular, the treatment to be performed, and the corresponding treatment identifier to be determined, can thereby already be entirely or at least partly established by way of the patient to be treated and his patient identifier.

In a further method step 314, one or more accessory set parameters are determined by means of the control system on the basis of an accessory database and at least on the basis of the treatment identifier of the treatment to be performed as well as preferably on the basis of the patient identifier, whereby the accessory set parameters characterize an accessory set of in particular one or more particularly suitable medical accessories for the treatment to be performed and preferably for the patient to be treated. The accessory database is additionally provided for the method 300 or as a part of the method 300, whereby the accessory database contains data sets on the plurality of medical accessories and is stored on a data storage apparatus of the control system.

A further method step 331 checks whether the accessory set parameters characterize at least one medical accessory of an accessory type which is not to be dosed, in particular because the medical accessories are of a non-dosable accessory type and/or have already been pre-dosed, pre-portioned and/or individually packaged—for instance cannulas, individually packaged adhesive tape sections or infusion tubes.

If process condition 305 is fulfilled; i.e. the accessory set parameters characterize at least one non-dosed medical accessory, a release mechanism designed to release medical accessories from at least one of the storage devices and which is data-linked to the control system is controlled in a further method step 316 on the basis of the accessory set parameters.

Lastly, in a further method step 318, the release mechanism in particular releases those non-dosed medical accessories for which at least one of the storage devices has storage areas for their accessory types and which are characterized by the accessory set parameter on which the control of the release mechanism is based.

In addition, a further method step 330 subsequent method step 314 checks whether the accessory set parameters characterize a medical accessory of a dosable accessory type, thus in particular an accessory type or a medical accessory respectively from which only a portion; i.e. only a specific dosage, is to be selected as well as released—for instance a liquid disinfectant or a section of an adhesive tape roll.

If process condition 303 is fulfilled; i.e. the accessory set parameters characterize a medical accessory of a dosable accessory type, one or more dosing parameters are determined in a further method step 332 which characterize the dosable medical accessory of the dosable accessory type and the required dosage for the accessory set.

A separating apparatus of a dosing apparatus having a storage area in which the dosable medical accessories are stored is thereupon controlled in a further method step 334 such that the separating apparatus extracts a portion of the at least one dosable medical accessory corresponding to the required dosage from the storage area and dispenses it to a supplying area.

While the preceding describes at least one preferential embodiment, it will be noted that there is a great number of variations thereof. It is also to be noted that the example embodiments described only represent non-limiting examples and are not thereby intended to limit the scope, the applicability or the configuration of the systems, apparatus and methods described herein. Rather, the foregoing description will provide a person skilled in the art with guidance for implementing at least one embodiment, wherein it is to be understood that a variety of changes can be made to the functioning and arrangement of the elements described in a preferential embodiment without thereby departing from the subject matter respectively set forth in the accompanying claims nor from legal equivalents thereof.

LIST OF REFERENCE NUMERALS

10 mobile selection system
20 control system
22 accessory database
24 data storage apparatus, particularly for the accessory database
26 data processing apparatus
28 working memory
30 communication device
31 communication device for treatment cart 100
32 data connection
50 user interface
52 user interface, particularly configured as treatment cart module
54 camera module, particularly configured as treatment cart module
66 individual involved in the treatment, particularly at treatment site 86, particularly patient or physician
80, 86, 88 treatment site
100, 160, 180 treatment cart
102 transport apparatus, particularly configured as treatment cart module
103 connecting device to power supply system
104 connecting apparatus for transport apparatus
108 repository device of treatment cart 100
110, 114, 118 storage device of treatment cart 100, particularly drawer
111 release mechanism for storage device 110
112 storage area of storage device 110
115 release mechanism for storage device 114
116 storage area of storage device 114
119 storage area of storage device 118
120 storage device of treatment cart 100, particularly compartment
121 release mechanism for storage device 120
122, 124, 126 storage area of storage device 120
130 drive apparatus of treatment cart 100
132 data bus
135 connecting unit of data bus 132
138 data storage apparatus for assistance information
144 connecting apparatus for treatment cart module
150 disposal apparatus
152 disposal bin 154 opening for objects to be disposed of, in particular medical accessories
156 locking mechanism for opening 154
158 weight/weight-change sensor system
162 wheel of treatment cart 160
163 electrical energy storage of treatment cart 160
166 detection system of treatment cart 160
168 repository device of treatment cart 160
170 storage device of treatment cart 160
171 release mechanism for storage device 170
172, 174, 176 storage areas of storage device 170
182 wheel of treatment cart 180
183 electrical energy storage of treatment cart 180
184 connecting apparatus for a user interface
190 storage device of treatment cart 180
191 release mechanism for storage device 190
192, 194, 196 storage areas of storage device 190
200 treatment cart module, in particular configured as a dosing apparatus
202 storage device of the dosing apparatus
203 storage area of storage device 202
204 separating apparatus of the dosing apparatus
206 dosing apparatus outlet
210 treatment cart module, in particular configured with a separating apparatus
212 chute of the separating apparatus of treatment cart module 210
213 segregating element
214 storage device of treatment cart module 210
215 storage area of storage device 214
216 opening for releasing a medical accessory to be selected
218 longitudinal axis of chute 212
220 treatment cart module, in particular configured as a glove box
222 chute of manual dispenser apparatus
224 medical accessory, in particular stored in the manual dispenser apparatus
226 opening for extraction of a medical accessory
228 longitudinal axis of chute 222
235 connecting unit for the data bus
244 connection point devices
300 method for selecting medical accessories
SA process start
SΩ process end
303 process condition: accessory set parameter characterizes a medical accessory of a closable accessory type
305 process condition: accessory set parameter characterizes at least one non-dosable medical accessory
310 to 334 method steps

The invention claimed is:

1. A mobile selection system for selecting medical accessories,
wherein the mobile selection system comprises:
a control system having an accessory database designed for data sets on a plurality of medical accessories and stored on a data storage apparatus of the control system;
a user interface designed for one or more inputs of a user, by means of which a treatment to be performed is specified and on the basis of which the control system determines a treatment identifier associated with the treatment to be performed as a result of said inputs;
a treatment cart comprising one or more storage devices, wherein the storage devices have at least two storage areas, each for a respective accessory type from among the plurality of medical accessories;
and wherein the control system is designed to implement a selection method comprising the following method steps:
determining the treatment identifier of the treatment to be performed; and
determining one or more accessory set parameters which characterize an accessory set of one or more suitable medical accessories for the treatment to be performed on the basis of the accessory database and at least on the basis of the treatment identifier of the treatment to be performed;
and wherein
the treatment cart comprises at least one release mechanism for releasing medical accessories and the control system is designed to control the at least one release mechanism on the basis of the accessory set parameters so as to release those medical accessories for which at least one of the storage devices comprises storage area for their respective type, and which are characterized by the accessory set parameters on which the control is based,
the treatment cart comprises a disinfectable work surface or a repository device having a disinfectable work surface, wherein the work surface is designed for the depositing of medical accessories and/or comprises one or more supplying areas for the segregation of medical accessories, and
the treatment cart comprises a disinfecting apparatus for the work surface, and the control system is designed to control the disinfecting apparatus for the work surface such that the disinfecting apparatus disinfects the work surface before, during and/or after the treatment to be performed and/or before, during and/or after specific treatment steps of the treatment to be performed.

2. The mobile selection system according to claim 1, wherein one of the storage devices comprises or consists of a drawer having one or more storage areas each for an accessory type of the plurality of medical accessories and the at least one release mechanism or a further release mechanism of the treatment cart for said storage device is designed to open the drawer.

3. The mobile selection system according to claim 1, wherein:
the at least one release mechanism or a further release mechanism of the treatment cart comprises or consists of a separating apparatus for one of the storage devices designed to segregate medical accessories out of at least one of the storage areas of said storage device; and
the control system is designed to control the separating apparatus on the basis of the accessory set parameter such that the separating apparatus withdraws at least one medical accessory out of the at least one storage area of said storage device and delivers it to a supplying area when the accessory set parameter characterizes such an medical accessory.

4. The mobile selection system according to claim 1,
wherein the treatment cart exhibits a dosing apparatus comprising one of the storage devices having at least one storage area for at least one medical accessory of a dosable accessory type and a separating apparatus for extracting a part of the at least one dosable medical accessory;
wherein the selection method further comprises the following method steps:
checking whether the accessory set parameters characterize a medical accessory of the dosable accessory type; and should this be the case, Determining one or more dosing parameters which characterize the dosable medical accessory and the required dosage for the accessory set;

wherein the control system is designed to control the separating apparatus of the dosing apparatus on the basis of the dosing parameter and such that the separating apparatus extracts a portion of the at least one dosable medical accessory corresponding to the required dosage from the at least one storage area of the dosing apparatus and dispenses it to a supplying area.

5. The mobile selection system according to claim 1, wherein:
the treatment cart comprises a connecting apparatus for treatment cart modules; and
the connecting apparatus is designed to establish a form-fit, force-fit and/or material-bond connection between the treatment cart and one or more treatment cart modules.

6. The mobile selection system according to claim 1, wherein the treatment cart comprises a connecting apparatus for a transport apparatus which is separable from said treatment cart.

7. The mobile selection system according to claim 1, wherein:
either the user interface is non-detachably connected to the treatment cart;
or the user interface is detachably connected or connectable to the treatment cart and/or the user interface, while designed for inputs as a consequence of which the control system determines the treatment identifier of the treatment to be performed, is positioned or positionable at a geographically different location than the location of the treatment cart.

8. The mobile selection system according to claim 1 which comprises at least one further treatment cart and wherein the mobile selection system comprises at least one further user interface and/or at least one of the user interfaces can be allocated to the treatment cart and the further treatment cart for inputs and to that end:
at least one of the user interfaces is non-detachably connected to one of the treatment carts and thus allocated to said treatment cart;
the mobile selection system comprises such a respective non-detachably connected user interface for each of the treatment carts which is thereby allocated to the respective treatment cart;
at least one of the user interfaces is detachably connected to one of the treatment carts and thus allocated to said treatment cart; and/or
the control system comprises an allocation rule for user interfaces and a data storage apparatus for same and said allocation rule is configured to allocate, based on allocation data stored in the data storage apparatus, a user interface characterized by means of a user interface identifier to a treatment cart characterized by means of a treatment cart identifier.

9. The mobile selection system according to claim 1, wherein the control system is designed to register the user as a function of successful system identification, determine a user identifier, execute the selection method and/or limit the selection or release of medical accessories to accessory types for which the registered user is authorized and/or, if the user is not successfully identified, not execute the selection process and/or limit the selection or release of medical accessories to accessory types for non-authorized users.

10. The mobile selection system according to claim 1, wherein:
one of the user interfaces is designed for one or more inputs of the user, by means of which the patient to be treated is specified and on the basis of which the control system determines a patient identifier associated with the patient to be treated as a result of said inputs;
the selection method further comprises the method steps of
determining the patient identifier of the patient to be treated; and
determining the accessory set parameter in the selection method on the basis of the treatment identifier and/or the patient identifier.

11. The mobile selection system according to claim 1, which further comprises a detection system for treatments which detects an individual involved in the treatment, a medical accessory and/or their arrangement and/or movement relative to each other by means of a sensor system operating based on measurement of radiation, ultrasound, weight and/or inertia and which determines on the basis of same a treatment performed and/or treatment step performed.

12. The mobile selection system according to claim 1, wherein the control system is designed to perform an assist process with at least the method step of determining one or more assistance parameters which characterize the treatment to be performed, a treatment step to be performed of the treatment to be performed, and/or a medical accessory for same.

13. A treatment cart for a mobile selection system according to claim 1, wherein the treatment cart comprises:
the user interface of the mobile selection system;
one or more storage devices, wherein the storage devices have at least two storage areas for medical accessories each of a respective accessory type;
at least one release mechanism for releasing medical accessories;
a drive apparatus comprising at least a part of the control system of the mobile selection system and/or a communication device for forming a data connection to the control system or another part of the control system respectively, wherein the drive apparatus for the control of the at least one release mechanism is thereby equipped by the control system to electrically actuate the at least one release mechanism on the basis of the accessory set parameter; and
a disinfectable work surface or a repository device having a disinfectable work surface, wherein the work surface is designed for the depositing of medical accessories and/or comprises one or more supplying areas for the segregation of medical accessories, and a disinfecting apparatus for the work surface, wherein
the drive apparatus for the control of the disinfecting apparatus for the work surface is thereby equipped by the control system to control the disinfecting apparatus for the work surface such that the disinfecting apparatus disinfects the work surface before, during and/or after the treatment to be performed and/or before, during and/or after specific treatment steps of the treatment to be performed.

14. The mobile selection system of claim 1, wherein said medical accessories is for cannulation of a patient blood vessels or for dialysis treatment.

15. The mobile selection system of claim 2, wherein said treatment cart is designed to extend out the drawer.

16. The mobile selection system of claim 4, wherein the control system is designed to control the separating apparatus on the basis of the accessory set parameter.

17. A method for the selection of medical accessories from among a plurality of medical accessories and thereby for releasing said medical accessories from a treatment cart having one or more storage devices, a disinfectable work surface or a repository device having a disinfectable work surface, wherein the work surface is designed for the depositing of medical accessories and/or comprises one or more supplying areas for the segregation of medical accessories, and a disinfecting apparatus for the work surface, wherein the medical accessories of the plurality of medical accessories are stored in at least two storage areas of the storage devices sorted according to their respective accessory types, which comprising the following method steps:

- detecting one or more user inputs, by means of which a treatment to be performed is specified, via a user interface which is data-linked to a control system;
- determining a treatment identifier of the treatment to be performed on the basis of said inputs via the control system;
- determining one or more accessory set parameters which characterize a medical accessory set of one or more medical accessories suitable for the treatment to be performed on the basis of an accessory database and at least on the basis of the treatment identifier of the treatment to be performed via the control system, wherein the accessory database comprises data sets on the plurality of medical accessories and is stored on a data storage apparatus of the control system;
- controlling a release mechanism which is designed to release medical accessories on the basis of the accessory set parameters from at least one of the storage devices and which is data-linked to the control system;
- releasing, via the release mechanism, those medical accessories for which the at least one of the storage devices exhibits storage area for their accessory types and which are characterized by the accessory set parameters on which the control of the release mechanism is based; and
- controlling the disinfecting apparats for the work surface by means of the control system such that the disinfecting apparatus disinfects the work surface before, during and/or after the treatment to be performed and/or before, during and/or after specific treatment steps of the treatment to be performed.

* * * * *